US010323926B2

(12) United States Patent
Elmaanaoui

(10) Patent No.: US 10,323,926 B2
(45) Date of Patent: Jun. 18, 2019

(54) CROSSTALK ELIMINATION OR MITIGATION IN OPTICAL COHERENCE TOMOGRAPHY

(71) Applicant: CANON U.S.A., INC., Melville, NY (US)

(72) Inventor: Badr Elmaanaoui, Belmont, MA (US)

(73) Assignee: Canon U.S.A., Inc., Melville, NY (US)

(*) Notice: Subject to any disclaimer, the term of this patent is extended or adjusted under 35 U.S.C. 154(b) by 31 days.

(21) Appl. No.: 15/629,175

(22) Filed: Jun. 21, 2017

(65) Prior Publication Data

US 2018/0372477 A1 Dec. 27, 2018

(51) Int. Cl.
*A61B 5/00* (2006.01)
*G01B 9/02* (2006.01)
*G01N 21/47* (2006.01)

(52) U.S. Cl.
CPC ........ *G01B 9/02091* (2013.01); *A61B 5/0066* (2013.01); *G01B 9/02001* (2013.01);
(Continued)

(58) Field of Classification Search
CPC ............ G01B 9/02091; G01B 9/02001; A61B 5/0066; G01N 2021/4797
See application file for complete search history.

(56) References Cited

U.S. PATENT DOCUMENTS 7,366,376 B2 4/2008 Shishkov et al.
7,382,464 B2 6/2008 Everett et al.
(Continued)

FOREIGN PATENT DOCUMENTS

EP 3127472 A1 2/2017
WO 2015117241 A1 8/2015
WO 2016/077252 A1 5/2016

OTHER PUBLICATIONS

Beaudette, K. et al., "Towards in vivo laser coagulation and concurrent optical coherence tomography through double-clad fiber devices", Proc. SPIE, Multimodal Biomedical Imaging XI, Mar. 7, 2016, vol. 9701.

(Continued)

*Primary Examiner* — Dominic J Bologna
(74) *Attorney, Agent, or Firm* — Canon U.S.A., Inc. I.P. Division

(57) ABSTRACT

One or more devices, systems, methods and storage mediums for performing optical coherence tomography (OCT) while reducing and/or eliminating crosstalk noise are provided. Examples of such applications include imaging, evaluating and diagnosing biological objects, such as, but not limited to, for Gastro-intestinal, cardio and/or ophthalmic applications, and being obtained via one or more optical instruments, such as, but not limited to, optical probes, catheters, capsules and needles (e.g., a biopsy needle). Preferably, the OCT devices, systems methods and storage mediums include or involve a method, such as, but not limited to, a complex conjugate method or a shift method, for handling the crosstalk noise in a way to mitigate or eliminate the noise from an image field of view. For example, a reference reflection or reference arm may be positioned or re-positioned in the image field of view at different locations depending on the crosstalk noise mitigation method being employed.

15 Claims, 12 Drawing Sheets

(52) U.S. Cl.
CPC ..... *G01B 9/02064* (2013.01); *G01N 21/4795* (2013.01); *G01N 2021/4797* (2013.01)

(56) References Cited

U.S. PATENT DOCUMENTS

| | | | |
|---|---|---|---|
| 7,843,572 B2* | 11/2010 | Tearney | A61B 5/0062 356/479 |
| 8,180,134 B2 | 5/2012 | Wang | |
| RE43,875 E | 12/2012 | Shishkov et al. | |
| RE45,142 E | 9/2014 | Kehrer et al. | |
| 8,928,889 B2 | 1/2015 | Tearney et al. | |
| 9,087,368 B2 | 7/2015 | Tearney et al. | |
| 9,332,942 B2 | 5/2016 | Jaffer et al. | |
| 9,435,956 B1 | 9/2016 | Xu et al. | |
| 9,513,276 B2 | 12/2016 | Tearney et al. | |
| 9,557,154 B2 | 1/2017 | Tearney et al. | |
| 2005/0165315 A1 | 7/2005 | Zuluaga et al. | |
| 2008/0262359 A1 | 10/2008 | Tearney et al. | |
| 2010/0092389 A1 | 4/2010 | Jaffer | |
| 2011/0292400 A1 | 12/2011 | Fleming et al. | |
| 2012/0057168 A1* | 3/2012 | Yuasa | A61B 3/102 356/479 |
| 2012/0101374 A1* | 4/2012 | Tearney | A61B 5/0066 600/427 |
| 2013/0003074 A1 | 1/2013 | Kurosaka | |
| 2015/0378105 A1 | 12/2015 | Godbout et al. | |
| 2016/0054113 A1* | 2/2016 | Osawa | G01B 9/02083 356/497 |
| 2016/0238532 A1 | 8/2016 | Freudiger et al. | |
| 2017/0135584 A1 | 5/2017 | Tearney et al. | |
| 2017/0209049 A1 | 7/2017 | Wang et al. | |

OTHER PUBLICATIONS

Dhalla, A. et al., "Crosstalk rejection in parallel optical coherence tomography using spatially incoherent illumination with partially coherent sources", Optics Letters, 2010, pp. 2305-2307, vol. 35, No. 13, abstract only.

Han, J. et al., "Effect of multimodal coupling in imaging micro-endoscopic fiber bundle on optical coherence tomography", Applied Physics B, Jan. 2012, pp. 635-643, vol. 106, No. 3, abstract only.

Yelin, D., et al, "Three-dimensional miniature endoscopy", Nature, Oct. 19, 2006, pp. 765, vol. 443.

Kathy Beaudette, et al., "Laser tissue coagulation and concurrent optical coherence tomography through a double-clad fiber coupler", Biomedical Optics Express, vol. 6, No. 4, Apr. 1, 2015, pp. 1293-1303, XP055499427, ISSN: 2156-7085, DOI: 10.1364/BOE. 6.001293, chapters 1, 2.3, 3.1.

Notification of Transmittal of International Search Report and the Written Opinion, and the International Search Report and Written Opinion, for PCT/US2018/028666, dated Aug. 30, 2018.

* cited by examiner

CROSSTALK ELIMINATION OR MITIGATION IN OPTICAL COHERENCE TOMOGRAPHY

FIELD OF THE INVENTION

The present disclosure relates generally to the field of optical imaging and more particularly to optical coherence tomography (OCT) devices, systems, methods and storage mediums using crosstalk elimination or mitigation. Examples of such applications include imaging, evaluating and diagnosing biological objects, such as, but not limited to, for gastro-intestinal, cardio and/or ophthalmic applications, and being obtained via one or more optical instruments, such as, but not limited to, one or more optical probes, one or more catheters, one or more endoscopes, one or more capsules, and one or more needles (e.g., a biopsy needle).

BACKGROUND OF THE INVENTION

Optical coherence tomography (OCT) is a technique for obtaining high resolution cross-sectional images of tissues or materials, and enables real time visualization. The aim of the OCT techniques is to measure the time delay of light by using an interference optical system or interferometry, such as via Fourier Transform or Michelson interferometers. A light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency. The frequency of the interference patterns corresponds to the distance between the sample arm and the reference arm. The higher frequencies are, the more the path length differences are.

Certain applications of OCT, such as multimodality OCT (MMOCT) or OCT/laser tissue coagulation, may make use of fibers with more than one clad in the sample arm and sometimes dual clad fiber couplers. When using double clad fibers (DCF), coherent detection suffers from crosstalk noise artifacts cause due to the use of DCF. Additionally, crosstalk between inner cladding modes and the core mode occurs at coupling interfaces causing image artifacts. Coupling interfaces include, but are not limited to, splices, connector to connector mates, and free space coupling from lens to lens or lens to fiber. The artifacts occur when inner cladding modes, excited at a primary crosstalk site, propagate within the inner cladding and couple back into the core at a secondary coupling site. Such issues may arise with other fiber configurations, such as, but not limited to, multi-clad fibers and fiber couplers.

To reduce crosstalk, current state of the art relies on two methods: (i) making fiber segments between coupling interfaces long enough such that crosstalk noise is deeper than the imaging range and cannot be seen; and (ii) attenuating the sample signal level such that crosstalk noise amplitude falls below a system noise floor and cannot be seen.

However, there are various issues related to these methods. For example, while making fiber segments between coupling interfaces longer in above method (i) may be manageable in a small subset of applications, this method may not be desirable for applications that, for example, require short probes or scanned probes. Making a probe unnecessarily longer can reduce its usability and increase its cost. Similarly for scanning probes like ones employed in luminal organ imaging like intravascular, lung, and GI tract the longer the probe the potentially worse the non-uniform rotational distortion (NURD) is and the substantially higher the background noise is. A higher background noise can make it harder to detect weak signals like Raman or autofluorescence from the sample.

By way of additional drawings of above method (ii), method (ii) relies on attenuating optical power to levels much lower than the maximum permissible power; limited mainly by a material's damage threshold or the maximum permissible exposure limit. Reducing power incident on the sample will reduce system sensitivity and therefore lower image penetration depth. This is usually undesirable since for most applications a goal is to maximize penetration depth in order to adequately visualize sub-surface structures deep within the sample. For weakly reflecting samples, this method may be detrimental for samples that have a combination of strong reflectors and weak reflectors since one would need to substantially reduce sample power level so as to have the crosstalk noise amplitude from strong reflectors fall below a system noise floor causing the signal from low reflecting structures to fall below the noise floor also or be barely visible. Strong reflectors may include stent struts embedded in the vessel wall, or air to sheath or lens to air interfaces in a catheter, endoscope, or capsule, among others. Weaker reflectors may include vessel wall subsurface structures like the media, intima, and adventitia in a coronary artery.

Accordingly, it would be desirable to provide at least one OCT technique and/or device for use in at least one optical device, assembly or system to avoid the aforementioned issues while mitigating crosstalk noise, especially in a way that reduces or minimizes cost of manufacture and maintenance.

SUMMARY OF THE INVENTION

Accordingly, it is a broad object of the present disclosure to provide OCT devices, systems, methods and storage mediums using an interference optical system, such as an interferometer (e.g., SD-OCT, SS-OCT, MMOCT, etc.), while mitigating, minimizing and/or adequately compensating for crosstalk noise. In accordance with one or more aspects of the present disclosure, cross-talk mitigation, minimization or compensation may be employed in double-clad fiber-based MMOCT devices or systems.

In accordance with one or more aspects of the present disclosure, there is no need to reduce system sensitivity or to use very long fiber segments (which, as aforementioned, may not be a possibility depending on a particular application). One or more embodiments of the present disclosure may also relax restrictions on core to core coupling efficiency and may match mode field diameter (MFD) at all coupling sites, which may be difficult for applications using a rotary junction for example.

In accordance with one or more aspects of the present disclosure, at least one embodiment of a multimodality optical coherence tomography system includes: an interference optical system that operates to: (i) receive and divide light from a light source into a first light with which an object or sample is to be irradiated and which travels along a sample arm of the interference optical system and a second reference light, (ii) send the second reference light along a reference arm of the interference optical system for reflection off of a reference reflection of the interference optical system, and (iii) generate interference light by causing reflected or scattered light of the first light with which the object or sample has been irradiated and the reflected second reference light to combine or recombine, and/or to interfere, with each other, the interference light generating one or more interference patterns; and at least one detector that operates to continuously acquire the interference light and/or the one or more interference patterns to measure the interference or the one or more interference patterns between the combined or recombined light.

In one or more embodiments, a crosstalk elimination or mitigation optical coherence tomography (OCT) system includes: an interference optical system that operates to: (i) receive and divide light from a light source into a first light with which an object or sample is to be irradiated and which travels along a sample arm of the interference optical system and a second reference light, (ii) send the second reference light along a reference arm of the interference optical system for reflection off of a reference reflection of the interference optical system, and (iii) generate interference light by causing reflected or scattered light of the first light with which the object or sample has been irradiated and the reflected second reference light to combine or recombine, and/or to interfere, with each other, the interference light generating one or more interference patterns; and at least one detector that operates to continuously acquire the interference light and/or the one or more interference patterns to measure the interference or the one or more interference patterns between the combined or recombined light, wherein the reference reflection is positioned in a field of view such that crosstalk noise is mitigated or eliminated from the field of view. In one or more embodiments, the OCT system is a multimodality OCT system and includes a double-clad fiber (DCF) segment, and the OCT system operates to eliminate or mitigate crosstalk induced image artifacts in coherent application(s) requiring use of the DCF segment.

In one or more embodiments (e.g., employing the complex conjugate technique discussed herein), the reference reflection may be positioned at, at about or around at least one of: a distal edge or an end of the field of view; and a distal edge or an end of the field of view such that an optical path length of the reference reflection is longer than a reflection or reflections of the object or sample and is situated at or at about a length of a maximum predetermined object or sample reflection.

A filter may be used to perform analog, digital or electronic filtering to eliminate or reduce any crosstalk noise that would otherwise alias into a predetermined signal frequency range. The filter may include at least one of: (i) a low pass filter to eliminate or reduce the aliasing; (ii) a high pass filter to eliminate or reduce direct current (DC) artifact(s); and (iii) a bandpass filter with a certain predetermined order for a low frequency cutoff and a certain order for a high frequency cutoff.

In one or more embodiments (e.g., employing the shift technique discussed herein), the reference reflection may be positioned at, at about or around at least one of: a position that is shorter than a predetermined or determined start of, or shorter than a proximal edge of, the field of view; a position that is shorter than a predetermined or determined start of, or shorter than a proximal edge of, the field of view such that an optical path length of the reference reflection is shorter than a first predetermined or determined sample reflection; and a position that is shorter than a predetermined or determined start of, or shorter than a proximal edge of, the field of view such that: (i) an optical path length of the reference reflection is shorter than a first predetermined or determined sample reflection, and (ii) the crosstalk noise wraps about a DC position and is no longer in a predetermined imaging range of the field of view. The reference reflection may be positioned such that about half of the crosstalk noise extends beyond the DC position, wraps around and is still away from a predetermined imaging range of the field of view and/or a predetermined image signal resulting in a crosstalk free region of an image of the object or sample. A crosstalk noise laden region of the image may be cropped (e.g., digitally) to have or obtain an image of the object or sample without any noise artifact(s). In one or more embodiments, at least one of the following may occur: (i) the cropped image may be further adjusted by putting black pixels where a DC artifact is or was and with a predetermined or determined number of pixels so as to have the object or sample appear with accurate dimensions in the image; (ii) the added pixels may be such that the pixels represent a lower range of intensities displayed in a same color map as the whole image; (iii) the added pixels may be such that the pixels have similar or the same characteristics as a background of the image; (iv) the similar or the same characteristics may include at least one of noise and speckle; and (v) a number of the added pixels may be such that, in response to using a catheter of a predetermined or determined dimension, an actual size measured from the image reflects an actual physical dimension of the catheter.

In at least one embodiment, at least one of following may exist: (i) the reference reflection comprises an anti-reflective (AR) coating, a high reflection (HR) coating, or a partial mirror; and (ii) the reference reflection allows for an improved or maximized signal-to-noise ratio (SNR).

An optical coherence tomography system may further include at least one of: (i) the light source that operates to produce the light; and (ii) a guide or waveguide for transmitting the light from the light source. An optical coherence tomography system may further include a deflecting section that operates to deflect the light from the light source to the interference optical system, and then send light received from the interference optical system towards the at least one detector. The deflecting section may include at least one of: one or more interferometers (e.g., a Michelson interferometer), a circulator, a beam splitter, an isolator, a coupler, a fusion fiber coupler, a partially severed mirror with holes therein, and a partially severed mirror with a tap. The reference arm may extend between the deflecting section and the reference reflection. The sample arm may extend between the deflecting section and the object or sample. In one or more embodiments, the reference arm may be spaced away from the object or sample, and the sample arm may extend between a portion of the reference arm and the object or sample. In one or more embodiments, the reference arm and the sample arm may overlap or share a common path between the deflecting section and the reference reflection; the sample arm may extend between the deflecting section and the object or sample; and/or the sample arm may extend via or through the reference reflection.

An optical coherence tomography system may further include an adjustment section that operates to control one or more relative optical characteristics between the first light having illuminated the object or sample and the reflected second light, wherein the deflecting section further operates to pass the light from the probe to the adjustment section and towards the at least one detector. An adjustment section may be used to position, re-position or adjust the reference reflection (and/or the reference arm) to mitigate or eliminate the crosstalk noise.

In one or more embodiments, an optical coherence tomography system may further include a catheter including a sheath, a coil, a protector and an optical probe, wherein: (i) the coil delivers torque from a proximal end to a distal end thereof; (ii) the coil is fixed with/to the optical probe so that a distal tip of the optical probe also spins to see an omnidirectional view of the object or sample being evaluated; (iii) the catheter is disposed at least in the sample arm; (iv) the optical probe is simultaneously translated longitudinally during the rotational spin resulting in a helical scanning pattern to acquire three-dimensional data of the object or sample; and (v) the translation is performed by pulling a tip of the optical probe back towards the proximal end.

An optical coherence tomography system may further include at least one processor that operates to process a signal from the at least one detector to acquire information of the object or sample.

In accordance with another aspect of the present disclosure, a method for performing crosstalk noise mitigation or elimination using an optical coherence tomography ("OCT") device or system having an interference optical system that operates to generate interference light and one or more interference patterns from a light that has been split into a first light with which an object or sample has been irradiated and a second reference light and having at least one detector, may include: positioning a reference reflection of the interference optical system in a field of view such that crosstalk noise is mitigated or eliminated from the field of view. The OCT device or system may be a multimodality OCT device or system and may include a double-clad fiber (DCF) segment, and the OCT device or system may operate to eliminate or mitigate crosstalk induced image artifacts in coherent application(s) requiring use of the DCF segment.

The positioning step may further include positioning the reference reflection at, at about or around at least one of: a distal edge or an end of the field of view; and a distal edge or an end of the field of view such that an optical path length of the reference reflection is longer than a reflection or reflections of the object or sample and is situated at or at about a length of a maximum predetermined object or sample reflection.

The method(s) may further include performing analog, digital or electronic filtering to eliminate or reduce any crosstalk noise that would otherwise alias into a predetermined signal frequency range. The filtering step may use at least one of: (i) a low pass filter to eliminate or reduce the aliasing; (ii) a high pass filter to eliminate or reduce direct current (DC) artifact(s); and (iii) a bandpass filter with a certain predetermined order for a low frequency cutoff and a certain order for a high frequency cutoff.

One or more embodiments of method(s) discussed herein may include positioning the reference reflection at, at about or around at least one of: a position that is shorter than a predetermined or determined start of, or shorter than a proximal edge of, the field of view; a position that is shorter than a predetermined or determined start of, or shorter than a proximal edge of, the field of view such that an optical path length of the reference reflection is shorter than a first predetermined or determined sample reflection; and a position that is shorter than a predetermined or determined start of, or shorter than a proximal edge of, the field of view such that: (i) an optical path length of the reference reflection is shorter than a first predetermined or determined sample reflection, and (ii) the crosstalk noise wraps about a DC position and is no longer in a predetermined imaging range of the field of view. The positioning of the reference reflection may be performed such that about half of the crosstalk noise extends beyond the DC position, wraps around and is still away from a predetermined imaging range of the field of view and/or a predetermined image signal resulting in a crosstalk free region of an image of the object or sample.

One or more methods discussed herein may include cropping a crosstalk noise laden region of the image digitally to have or obtain an image of the object or sample without any noise artifact(s). In one or more embodiments, at least one of the following may occur: (i) the cropped image is further adjusted by putting black pixels where a DC artifact is or was and with a predetermined or determined number of pixels so as to have the object or sample appear with accurate dimensions in the image; (ii) the added pixels are such that the pixels represent a lower range of intensities displayed in a same color map as the whole image; (iii) the added pixels are such that the pixels have similar or the same characteristics as a background of the image; (iv) the similar or the same characteristics include at least one of noise and speckle; and (v) a number of the added pixels is such that, in response to using a catheter of a predetermined or determined dimension, an actual size measured from the image reflects an actual physical dimension of the catheter.

One or more methods may further include at least one of: (i) sending the second reference light along a reference arm of the interference optical system for reflection off of the reference reflection of the interference optical system; (ii) receiving the light from a light source; (iii) splitting the light from the light source into the first light and the second reference light to generate the interference light; and (iv) acquiring, via the at least one detector, the interference light and/or the one or more interference patterns to measure the interference or the one or more interference patterns. In one or more embodiments, the reference arm may overlap with at least a portion of a sample arm of the interference optical system. The first light travels along a sample arm of the interference optical system.

In accordance with a further aspect of the present disclosure, a computer-readable storage medium may be used for storing a program that operates to cause one or more processors to perform a method for performing crosstalk noise mitigation or elimination using an OCT device or system having an interference optical system that operates to generate interference light and one or more interference patterns from a light that has been split into a first light with which an object or sample has been irradiated and a second reference light and having at least one detector, the method comprising: positioning a reference reflection of the interference optical system in a field of view such that crosstalk noise is mitigated or eliminated from the field of view. As aforementioned, the OCT device or system may be a multimodality OCT device or system, may include a double-clad fiber (DCF) segment, and may operate to eliminate or mitigate crosstalk induced image artifacts in coherent application(s) requiring use of the DCF segment. The reference reflection may be positioned as described herein in one or more embodiments.

In accordance with at least another aspect of the present disclosure, the OCT technique(s) discussed herein may be employed to reduce the cost of at least one of manufacture and maintenance of OCT devices, systems and storage mediums by reducing or minimizing a number of optical components in an interference optical system, such as an interferometer. A probe may include a reference arm and a sample arm, and may include an optical fiber and other optical materials. In one or more embodiments, the reference arm and the sample arm may be included in a probe housing to prevent path length mismatches, dispersion mismatches and/or polarization mismatches while making one or more measurements.

In accordance with yet a further aspect of the present disclosure, regular probes, as well as common path probe(s), are provided for OCT (e.g., SS-OCT, SD-OCT, MMOCT, etc.). One or more differences between regular probes and common path probes may relate to a specific coating on the single reference surface.

According to other aspects of the present disclosure, one or more additional devices, one or more systems, one or more methods and one or more storage mediums using OCT are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein:

FIGS. 4(a)-5(d) are reflectivity profile graphs, without and with crosstalk noise, respectively, for at least one embodiment of a method for obtaining an image for use with at least one OCT device or system in accordance with one or more aspects of the present disclosure;

FIGS. 6(a)-7(d) are reflectivity profile graphs, without and with crosstalk noise, respectively, for at least one embodiment of a complex conjugate method for use with at least one OCT device or system in accordance with one or more aspects of the present disclosure;

FIGS. 9(a)-10(d) are reflectivity profile graphs, without and with crosstalk noise, respectively, for at least one embodiment of a shift method for use with at least one OCT device or system in accordance with one or more aspects of the present disclosure;

DETAILED DESCRIPTION OF THE PRESENT INVENTION

One or more devices, optical systems, methods and storage mediums for performing imaging using an OCT technique are disclosed herein. In accordance with at least one aspect of the present disclosure, one or more devices, optical systems, methods and storage mediums discussed herein use an OCT technique to remove or mitigate crosstalk noise, including, in one or more embodiments, in double clad fiber-based (DCF-based) multimodality OCT devices or systems.

Figure 1:
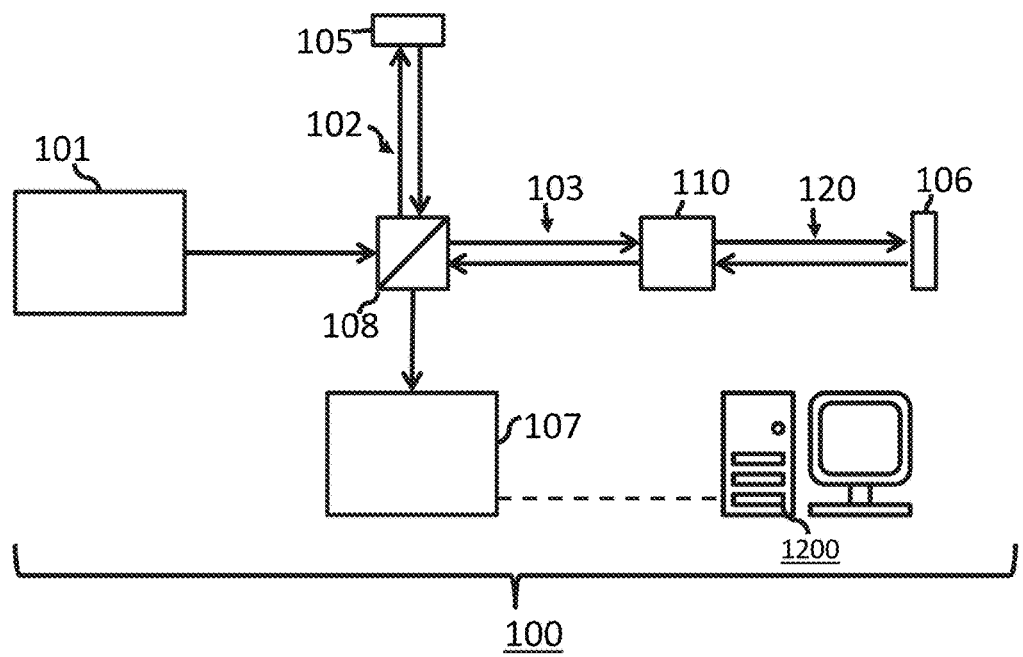
FIG. 1 is a diagram showing an embodiment of a system which can utilize crosstalk elimination or mitigation OCT technique(s) with optical probe applications in accordance with one or more aspects of the present disclosure.
Figure 2:
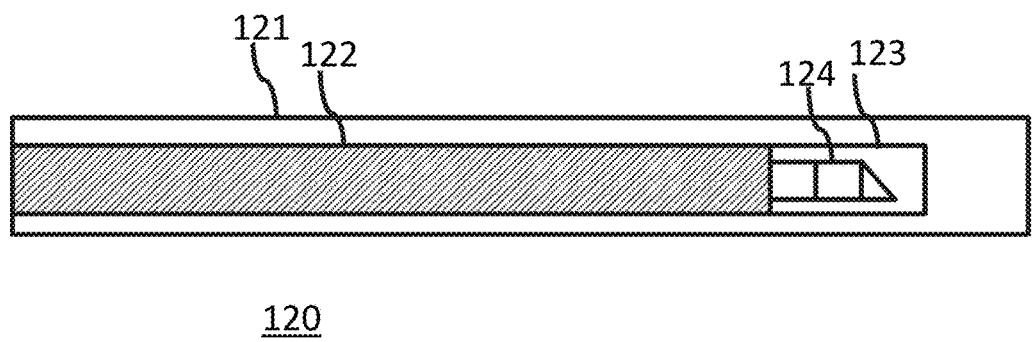
FIG. 2 is a diagram of an embodiment of a catheter that may be used with at least one embodiment of a crosstalk reduction or elimination OCT technique with optical probe applications in accordance with one or more aspects of the present disclosure.

Turning now to the details of the figures, FIG. 1 shows an OCT system 100 (as referred to herein as "system 100" or "the system 100") which operates to utilize an OCT technique with optical probe applications in accordance with one or more aspects of the present disclosure. The system 100 comprises a light source 101, a reference arm 102, a sample arm 103, a deflected or deflecting section 108, a reference mirror (also referred to as a "reference reflection", "reference reflector", "partially reflecting mirror" and a "partial reflector") 105, and one or more detectors 107. In one or more embodiments, the system 100 may include a patient interface device or unit ("PIU") 110 and a catheter 120 (as diagrammatically shown in FIG. 1; an embodiment example is shown in FIG. 2 and discussed further below), and the system 100 may interact with a sample 106 (e.g., via the catheter 120 and/or the PIU 110). In one or more embodiments, the system 100 includes an interferometer or an interferometer is defined by one or more components of the system 100, such as, but not limited to, at least the light source 101, the reference arm 102, the sample arm 103, the deflecting section 108 and the reference mirror 105.

The light source 101 operates to produce a light to the deflecting section 108, which splits the light from the light source lox into a reference beam passing into the reference arm 102 and a sample beam passing into the sample arm 103. The deflecting section 108 may be positioned or disposed at an angle to the reference mirror 105, the one or more detectors 107 and to the sample 106. The reference beam is reflected from the reference mirror 105 in the reference arm 102 while the sample beam is reflected or scattered from a sample 106 through the PIU (patient interface unit) 110 and the catheter 120 in the sample arm 103. Both of the reference and sample beams combine (or recombine) at the deflecting section 108 and generate interference patterns. The output of the system 100 and/or the interferometer thereof is continuously acquired with the one or more detectors 107, e.g., such as, but not limited to, photodiodes or multi-array cameras. The one or more detectors 107 measure the interference or interference patterns between the two radiation or light beams (e.g., a reference beam from the reference arm 102 and a sample beam from the sample arm 103) that are coupled, combined or recombined. In one or more embodiments, the reference and sample beams have traveled different optical path lengths such that a fringe effect is created and is measurable by the one or more detectors 107. Electrical analog signals obtained from the output of the system 100 and/or the interferometer thereof are converted to digital signals to be analyzed with a computer, such as, but not limited to, the computer 1200 (see FIG. 1; also shown in FIG. 13 discussed further below), the computer 1200' (see e.g., FIG. 14 discussed further below), etc. In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

Preferably, the deflected section 108 operates to deflect (or split) the light from the light source 101 to the reference and sample arms 102, 103 to the reference mirror 105 and the sample 106, respectively, and then combine or recombine the light and send the combined or recombined light received from the reference mirror 105 and the sample 106 towards the at least one detector 107. In one or more embodiments, the deflected section 108 of the system 100 may include or may comprise one or more interferometers or optical interference systems that operate as described herein, including, but not limited to, a circulator, a beam splitter (see e.g., FIG. 1), an isolator, a coupler (e.g., fusion fiber coupler), a partially severed mirror with holes therein, a partially severed mirror with a tap, etc. In one or more embodiments, the interferometer or the optical interference system may include one or more components of the system 100, such as, but not limited to, one or more of the light source 101, the reference arm 102, the sample arm 103, the deflected section 108 and/or the reference reflection 105. In one or more embodiments, the deflected or deflecting section 108 may include common path components, such as, but not limited to, a common path interferometer, a common path optical interference system, etc.

In one or more embodiments of an interferometer (e.g., a Michelson interferometer), a light source, such as the light source lot, operates to produce a light to a splitter, which splits the light from the light source lot into a reference beam passing into a reference arm and a sample beam passing into a sample arm, which may be physically separate arms. In such an interferometer, a deflection section (such as the deflection section 108, which may be a beam splitter or other suitable component as described hereinabove) may be positioned or disposed at an angle to a reference mirror (such as the reference mirror 105), at least one detector (such as the detector 107) and to a sample (such as the sample 106). The reference beam is reflected from a reference mirror (such as the reference reflection 105) in the reference arm while the sample beam is reflected or scattered from a sample (such as the sample 106) in the sample arm.

In one or more embodiments, the reference reflector or reference reflection 105 may be disposed in the system 100 at least one of: (i) at the start of the image field of view (FOV) or at a proximal edge of imaging (see e.g., FIGS. 4(a)-5(d) discussed further below); (ii) at a distal edge of imaging or at the end of the image FOV (see e.g., FIGS. 6(a)-7(d) discussed further below); and (iii) at a position that is shorter than a predetermined or desired start of the image FOV (see e.g., FIGS. 9(a)-10(d) discussed further below). Preferably, when employing the complex conjugate method (discussed further below), the reference reflector or reference reflection 105 is disposed at the end of the image FOV or at a distal edge of imaging. Preferably, when employing the shift method (discussed further below), the reference reflector or reference reflection 105 is disposed at the position that is shorter than the predetermined or desired start of the image FOV. One or more embodiments may include an adjustment section or component that permits the reference reflection 105 to be positioned (or re-positioned) along the reference arm 102 depending on the method selected to reduce or mitigate crosstalk noise (see e.g., adjustment section 904 in FIG. 12A discussed further below). In one or more embodiments, the reference reflection 105 may interact with one or more discrete reflectors (see e.g., the three discrete reflectors as shown in each of FIGS. 4(a), 5(a), 6(a), 7(a), 9(a) and 10(a) as discussed below).

One application of an OCT technique of the present disclosure is to use the technique with a catheter 120 as schematically shown in FIG. 1. FIG. 2 shows an embodiment of the catheter 120 including a sheath 121, a coil 122, a protector 123 and an optical probe 124. As shown schematically in FIG. 1, the catheter 120 preferably is connected to the PIU 110 to spin the coil 122 with pullback (e.g., at least one embodiment of the PIU 110 operates to spin the coil 122 with pullback). The coil 122 delivers torque from a proximal end to a distal end thereof. In one or more embodiments, the coil 122 is fixed with/to the optical probe 124 so that a distal tip of the optical probe 124 also spins to see an omnidirectional view of a biological organ, sample or material being evaluated, such as, but not limited to, hollow organs such as vessels, a heart, etc. For example, fiber optic catheters and endoscopes may reside in the sample arm (such as the sample arm 103 as shown in FIG. 1) of an OCT interferometer in order to provide access to internal organs, such as intravascular images, gastro-intestinal tract or any other narrow area, that are difficult to access. As the beam of light through the optical probe 124 inside of the catheter 120 or endoscope is rotated across the surface of interest, cross-sectional images of one or more samples are obtained. In order to acquire three-dimensional data, the optical probe 124 is simultaneously translated longitudinally during the rotational spin resulting in a helical scanning pattern. This translation is most commonly performed by pulling the tip of the probe 124 back towards the proximal end and therefore referred to as a pullback.

In one or more embodiments, the patient user interface 110 may comprise or include a connection component (or interface module), such as a rotary junction, to connect one or more components, such as one or more components of a probe (e.g., a catheter 120 (see e.g., FIGS. 1-2)), a needle, a capsule, a patient interface unit (e.g., the patient interface unit 110), etc., to one or more other components, such as, an optical component, a light source (e.g., the light source 101), a deflection section (e.g., the deflection or deflected section 108), the sample arm 102, a motor that operates to power the connection component and/or the patient user interface 110 (e.g., one or more motors may be used to control pullback, to control spin or rotation, etc.), etc. For example, when the connection member or interface module is a rotary junction, the rotary junction may be at least one of: a contact rotary junction, a lenseless rotary junction, a lens-based rotary junction, or other rotary junction known to those skilled in the art.

In Fourier domain optical coherence tomography (FDOCT), an approximation of the sample reflectivity profile, $r_S(z_S)=\sqrt{R_S(z_S)}$, may be reconstructed by processing the Fourier analysis (e.g., the Fast Fourier Transform) of the wavelength dependent detector current $I_D(k)$, where k is the wavenumber and is related to wavelength, $\lambda$, such that $k=2\pi/\lambda$. In spectral domain optical coherence tomography (SD-OCT) spectral components $I_D(k)$ may be captured simultaneously by an array detector at the output of a spectrometer as the light is emitted from a continuous wave broadband light source. In swept source optical coherence tomography (SS-OCT) spectral components $I_D(k)$ may be captured sequentially by a single detector as the wavelength of a narrowband light source is rapidly swept in time. Although the process of capturing $I_D(k)$ depends on the type of FDOCT method, the sample reflectivity profile $r_S(z_S)$ is estimated from $i_D(z)$ in a similar way, where $i_D(z)$ is the inverse Fourier Transform of $I_D(k)$ and is given by Equation 1, as follows:

$$i_D(z) = \frac{\rho}{8}[\gamma(z)[R_R + R_{S1} + R_{S2} + \ldots\ ]]\qquad \text{``DC Terms''}$$

$$+ \frac{\rho}{4}\left[\gamma(z) \otimes \sum_{n=1}^{N} \sqrt{R_R R_{Sn}}\ (\delta(z \pm 2(z_R - z_{Sn})))\right]\quad \text{``Cross-correlation Terms''}$$

$$+ \frac{\rho}{8}\left[\gamma(z) \otimes \sum_{n \neq m=1}^{N} \sqrt{R_{Sn} R_{Sm}}\ (\delta(z \pm 2(z_{Sn} - z_{Sm})))\right]\quad \text{``Auto-correlation Terms''}$$

The sample reflectivity profile $r_S(r_S)=\sqrt{R_S(z_S)}=\sum_{n=1}^{N}\sqrt{R_{Sn}}\delta(z_S-z_{Sn})$ is embedded in the cross-correlation terms of Equation 1. Equation 1 is further simplified to obtain an "A-scan" or OCT depth profile and is given by Equation 2, as follows:

$$i_D(z) = \frac{\rho}{8}[\gamma(z)[R_R + R_{S1} + R_{S2} + \ldots\ ]]\qquad \text{``DC Terms''}$$

$$+ \frac{\rho}{4}\sum_{n=1}^{N}\sqrt{R_R R_{Sn}}\ [\gamma[2(z_R - z_{Sn})] + \gamma[-2(z_R - z_{Sn})]]\quad \text{``Cross-correlation Terms''}$$

$$+ \frac{\rho}{8}\sum_{n \neq m=1}^{N}\sqrt{R_{Sn} R_{Sm}}\ [\gamma[2(z_{Sn} - z_{Sm})] + \gamma[-2(z_{Sn} - z_{Sm})]]\quad \text{``Auto-correlation Terms''}$$

As can be seen from Equation 2, the sample field reflectivity profile $r_S(z_S)$ is reproduced in the cross-correlation terms with the zero position of the reflectivity profile being at the position of the reference reflector $z_R$, with the sample reflector displacement doubled since the interferometer measures the round-trip distance from the reflector, and with the sample reflectors blurred through the convolution with the coherence function $\gamma(z)$, which in the case of a Gaussian spectrum is given by $\gamma(z)=e^{-z^2\Delta k^2}$.

As seen in the cross-correlation terms, a mirror image of the modified reflectivity profile appears on the opposite ends of the reference reflector. This effect, referred to as the complex conjugate effect, comes from the fact that the inverse Fourier transform of the detected real signal must be Hermitian symmetric in one or more embodiments. Hence positive and negative distances relative to the reference distance are complex conjugates of each other and in this case identical since the detected signal is by necessity real.

FIGS. 4(a)-4(d) illustrate the results of equations 1 and 2 for the example of discrete sample reflectors (e.g., exemplary sample reflectivity profile of three discrete reflectors with the reference reflection at the start of image field of view (FOV) (see FIGS. 4(a)-4(b))) and a Gaussian-shaped spectrum in the absence of crosstalk noise. By way of example and for illustrative purposes, FIGS. 4(a)-4(d) ignore or do not include auto-correlation terms. Also, since for many applications the reference reflectivity is much larger than any sample reflectivity, the amplitude of the auto-correlation terms may be much smaller than the cross-correlation terms. FIG. 4(c) shows an A-scan from a Fourier domain low coherence interferometry in the absence of crosstalk. FIG. 4(d) shows a resultant A-scan in the absence of crosstalk.

Although several examples discussed herein will focus on double clad fibers (DCF), features of the present disclosure are applicable to other fibers, such as, but not limited to, multi-clad fibers and fiber couplers, as well. In one or more embodiments, the DCF core is usually used for OCT single mode excitation and coherent detection whereas the cladding is used for fluorescence detection or coagulation energy delivery among other uses depending on the application. Using DCF in one or more applications is beneficial since the use of DCF allows for a simplified light delivery and co-localization of the different modality signals.

As aforementioned, crosstalk between inner cladding modes and the core mode may occur at coupling interfaces causing image artifacts. Coupling interfaces include, but are not limited to, splices, connector to connector mates, and free space coupling from lens to lens or lens to fiber. The artifacts occur when inner cladding modes, excited at a primary crosstalk site propagate within the inner cladding and couple back into the core at a secondary coupling site. Light travelling through the inner cladding accumulates a phase shift compared to light travelling through the core then interferes with the reference arm creating several undesired attenuated replicas of the sample image shifted by $\Delta L_m$ with respect to the main image, where m stands for the different cladding modes with delay for each cladding mode given by $\Delta L_m = \Delta n_m \cdot l_{DCF} \cdot l_{DCF}$ is the physical distance traveled and $\Delta n_m = n_{core\_eff} - n_{m,clad\_eff}$ is the refractive index difference between the effective refractive index of a particular inner cladding mode, $n_{m,clad\_eff}$, and that of the fundamental core mode, $n_{core\_eff}$.

Since inner cladding modes have a lower effective index of refraction than the fundamental core mode, crosstalk artifacts appear at shorter path lengths than the sample signal. Moreover, lower cladding modes with lower effective indices of refraction appear at shorter path lengths than higher cladding modes since they travel a smaller path within the same cladding material (i.e., same index of refraction, $n_{clad}$). By way of example, for a DCF fiber segment 1.5 meters long and 0.5 clad numerical aperture (NA) at about 1.3 microns wavelength with a cladding radius of about 62.5 microns several thousand modes may exist in the inner clad. For $\Delta n_m = \sim 0.001$- to $\sim 0.003$ these thousands of inner cladding modes may accumulate an optical path length delay of about 1.5 mm to 4.5 mm each way (for a single pass) of the double pass process. In other words, the total length delay may be about 3 mm to 9 mm total distance, which corresponds to the depth offset or delay of 1.5 mm to 4.5 mm.

OCT excitation through the core has typically low NA and hence collects mostly ballistic and quasi-ballistic photons through the core. For one or more applications utilizing SMF in the sample path, most multiply scattered photons are rejected due to the low NA and small aperture size of the core. However, when DCF is/are used, multiply scattered photons and some single or quasi-singly scattered photons may get collected through the large clad aperture and high NA. This is especially true of highly scattering media.

Light collected within the clad tends to be biased more towards lower cladding modes given that OCT excitation is through the low NA core and intensity of light collected at the inner cladding tends to decrease with increasing acceptance angle. Also, specular reflection, which in many applications tends to be the source of the strongest signals in the image, subtends smaller angles and is therefore mostly collected through the core and the lower inner cladding modes.

Figure 4:
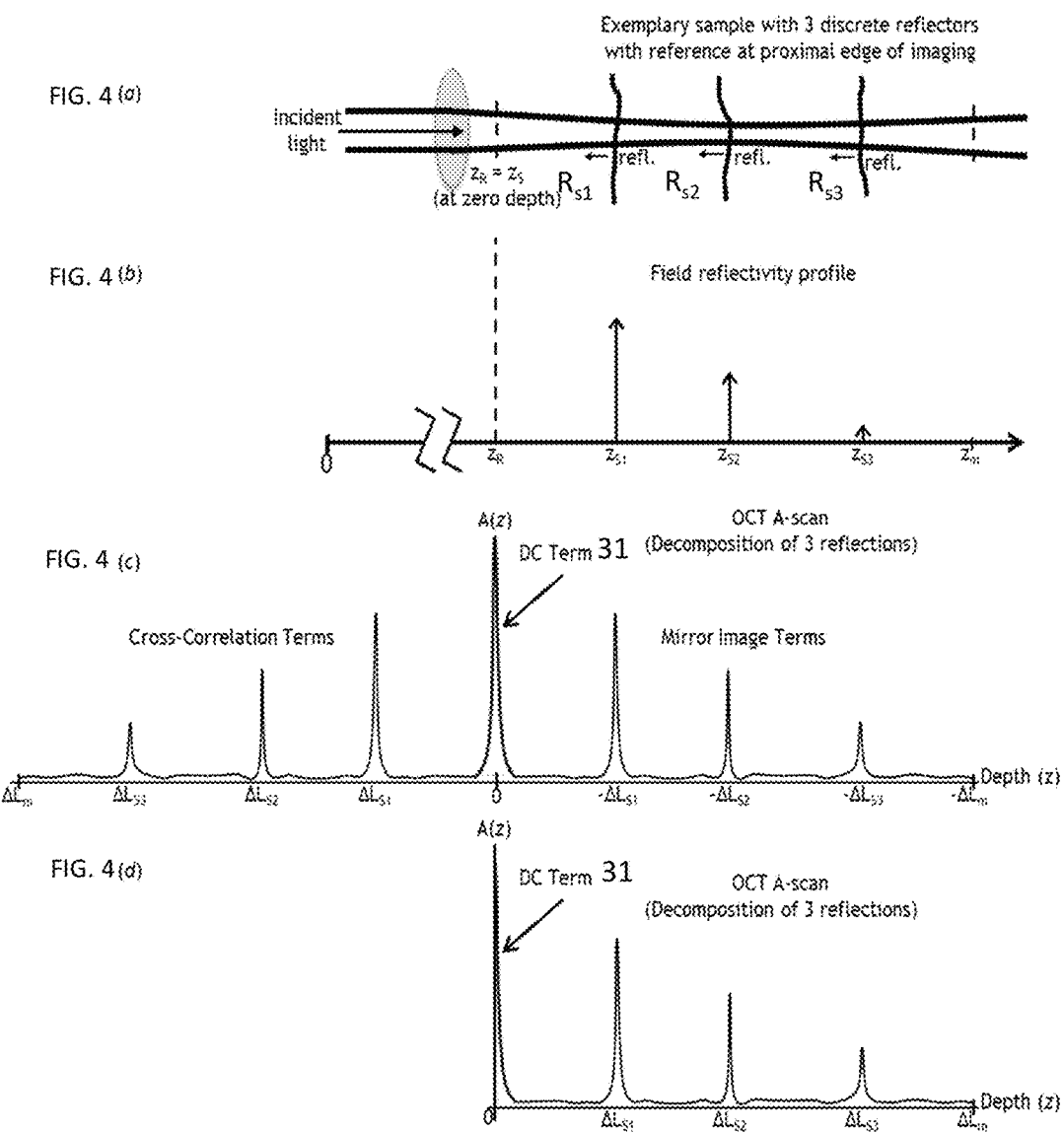
Figure 5:
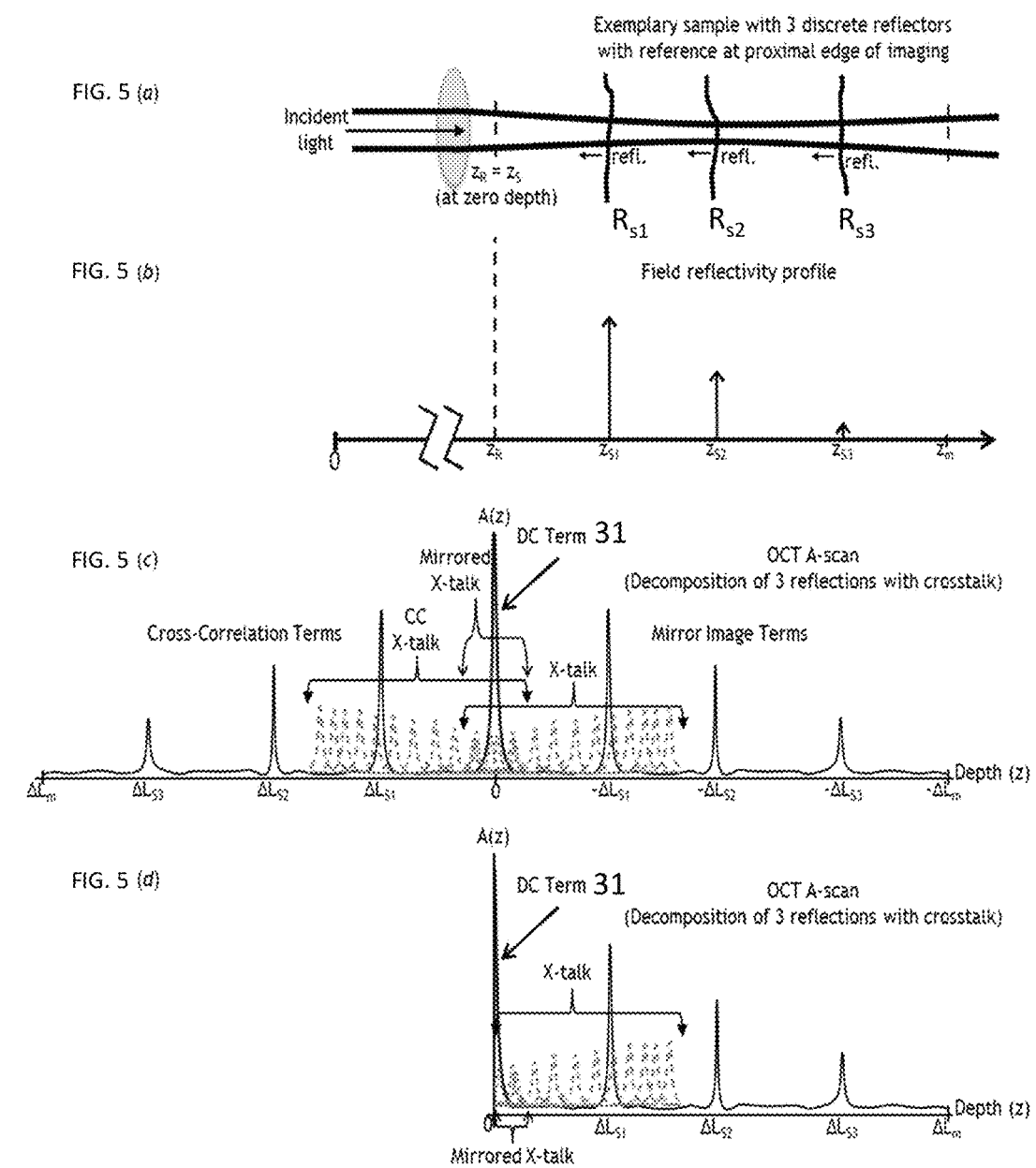

When the reference reflector is placed at the start of the desired imaging field of view (FOV), as is the case in FIGS. 4(a)-5(d) (see e.g., FIG. 4(a) and FIG. 5(a)), shallower depths appear closer to the zero-path or DC position 31 and deeper structures appear further from the zero-path position for cross-talk noise (see e.g., FIGS. 5(a)-5(d)). FIGS. 5(a)-5(d) depict the same example of discrete sample reflectors and Gaussian spectrum as FIGS. 4(a)-4(d) when DCF is used (i.e., FIGS. 5(a)-5(d) show an exemplary sample reflectivity profile having three discrete reflectors with the reference reflection at the start of image FOV (see FIGS. 5(a) and 5(b)), an A-scan from the Fourier domain low coherence interferometry in the presence of crosstalk (FIG. 5(c)) and a resultant A-scan in the presence of crosstalk (FIG. 5(d)), and shows when crosstalk noise is manifest. FIG. 5(c) shows crosstalk (also referred to herein as "X-talk") from the strong sample reflector $R_{S1}$ (e.g., a first reflection/reflector value of the sample; a first reflection value of the sample at a first predetermined position relative to the sample based on the optics being used; etc.) spanning a large depth range and crossing the zero-path position or DC position 31 as well as a much weaker crosstalk noise from $R_{S2}$ (e.g., a second reflection/reflector value of the sample; a second reflection value of the sample at a second predetermined position relative to the sample based on the optics being used; etc.) spanning a much narrower range at about DC since most of it is below the noise floor. Crosstalk from $R_{S3}$ (e.g., a third reflection/reflector value of the sample; a third reflection value of the sample at a third predetermined position relative to the sample based on the optics being used; etc.) is so small that all of it is below the noise floor. The resultant A-scan, FIG. 5(d), depicts the desired signal with overlapping crosstalk noise spanning a considerable portion of the image FOV. In or more embodiments, $Z_R$ (reference reflection depth) may be positioned at the reference reflection or reflector 105. $R_{S1}$ and $R_{S2}$ may be located at the sample 106, and $Z_S$ may be located at the beginning of the sample 106. $R_{S1}$, $R_{S2}$, and $R_{S3}$, in at least one embodiment, are located inside the sample 106, and are longer than $Z_S$ (e.g., start of the sample; proximal sample depth; smallest sample depth; etc.) located at the beginning of the sample 106. In one or more embodiments, $Z_R$ and $Z_S$ may be equal to each other, for example, $Z_R = Z_S = 1$ meter. In one or more embodiments, $Z_R = Z_S$+depth, for example, $Z_R = Z_S + 5$ mm. By way of another example of one or more embodiments, $Z_R = Z_S = 1$ meter-2 mm. The movement or positioning of one or more of $Z_R$, $Z_S$, $R_{S1}$, $R_{S2}$ and $R_{S3}$ may vary depending on the method employed, e.g., the complex conjugate method, the shift method, etc.

Figures 3A, 3B:
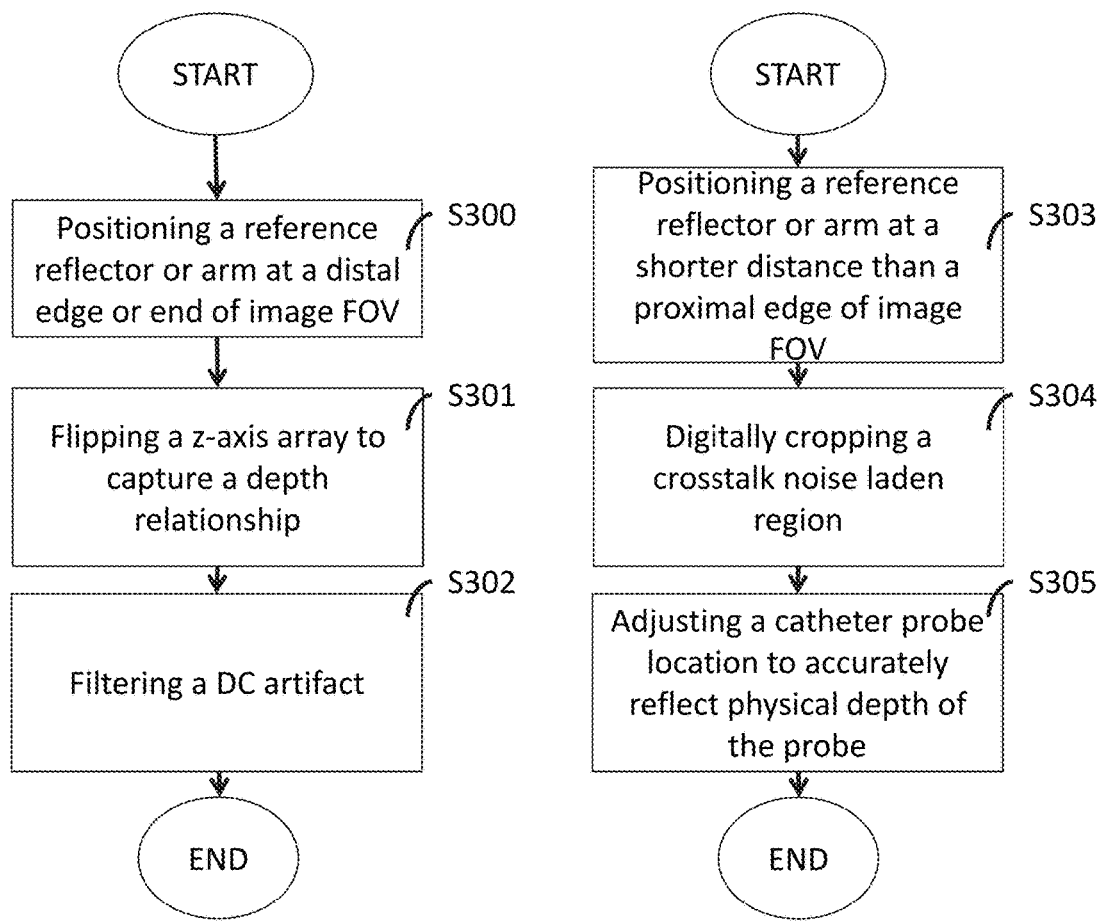
FIGS. 3(a)-3(b) are flowcharts for at least one respective embodiment of a complex conjugate method and a shift method, respectively, for use with at least one OCT device or system in accordance with one or more aspects of the present disclosure.

In accordance with another aspect of the present disclosure and as aforementioned, one or more methods for performing signal processing are provided herein to reduce or mitigate crosstalk noise. FIGS. 3(a) and 3(b) illustrate flow charts of a complex conjugate method and a shift method, respectively, for reducing or mitigating crosstalk noise in an image(s). Preferably, the complex conjugate method(s) may include one or more of the following: (i) positioning or providing a reference reflector (such as the reference reflector 105) (or reference arm) at a distal edge or an end of an image field of view (FOV) (see step S300 of FIG. 3(a)); (ii) flipping a z-axis array to capture a depth relationship (see step S301 of FIG. 3(a)); and (iii) performing filtering as needed (e.g., filtering a DC artifact (see e.g., step S302 of FIG. 3(a))). Preferably, the shift method(s) may include one or more of the following: (i) positioning or providing a reference reflector (such as the reference reflector 105) (or reference arm) at a shorter distance than the proximal edge of the image field of view (FOV) (see step S303 of FIG. 3(b)); digitally cropping a crosstalk noise laden region of the image (see step S304 of FIG. 3(b)); and (iii) adjusting a catheter probe location to accurately reflect physical depth of the probe (see step S305 of FIG. 3(b)). Additional details for each of the complex conjugate method(s) and the shift method(s) are discussed below and shown in the figures, such as FIGS. 4(a)-11(f), of the present disclosure. In one or more embodiments, filtering (e.g., step S302) may be omitted when not needed.

First Embodiment—Complex Conjugate Method

Figure 6:
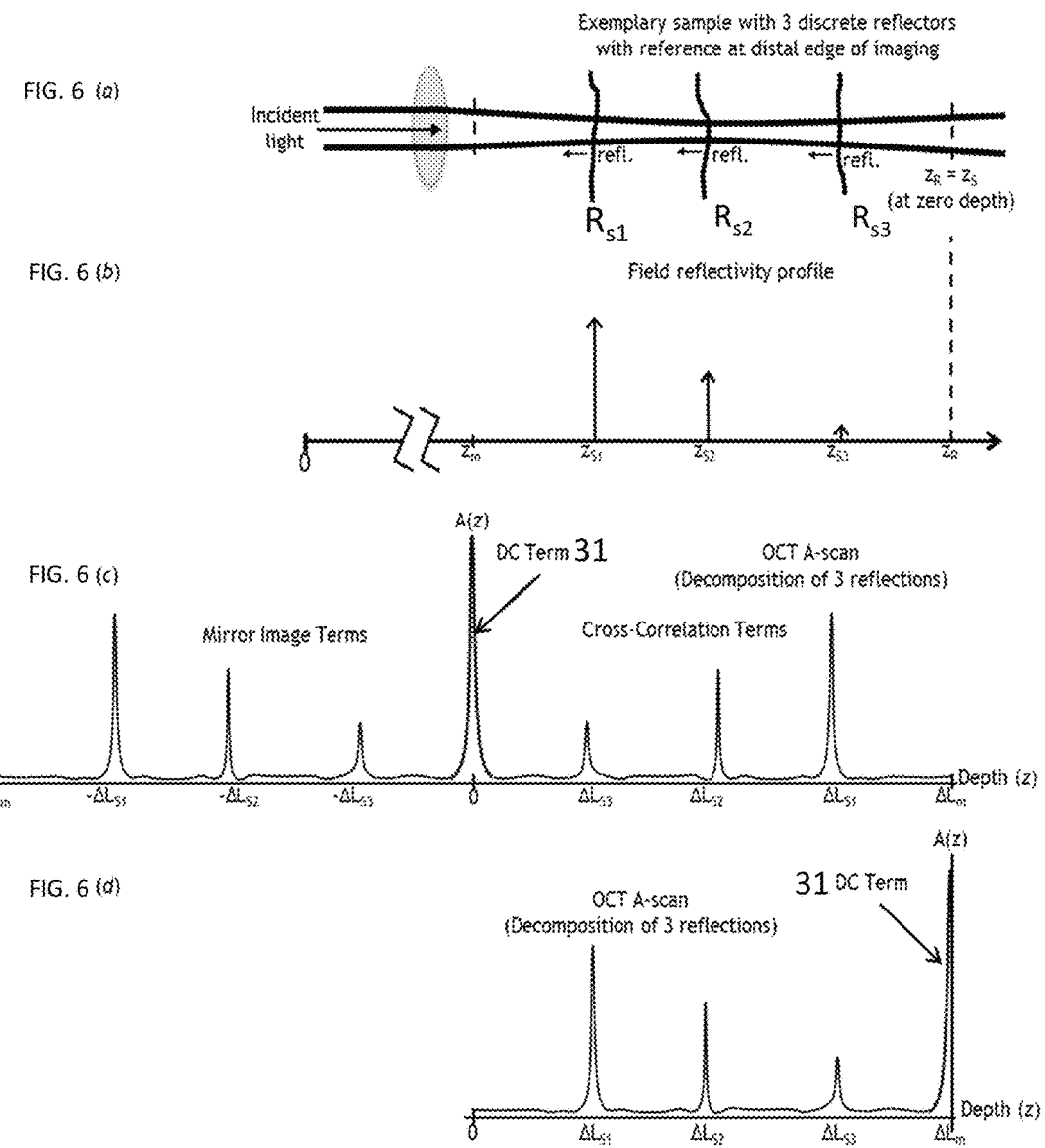
Figure 7:
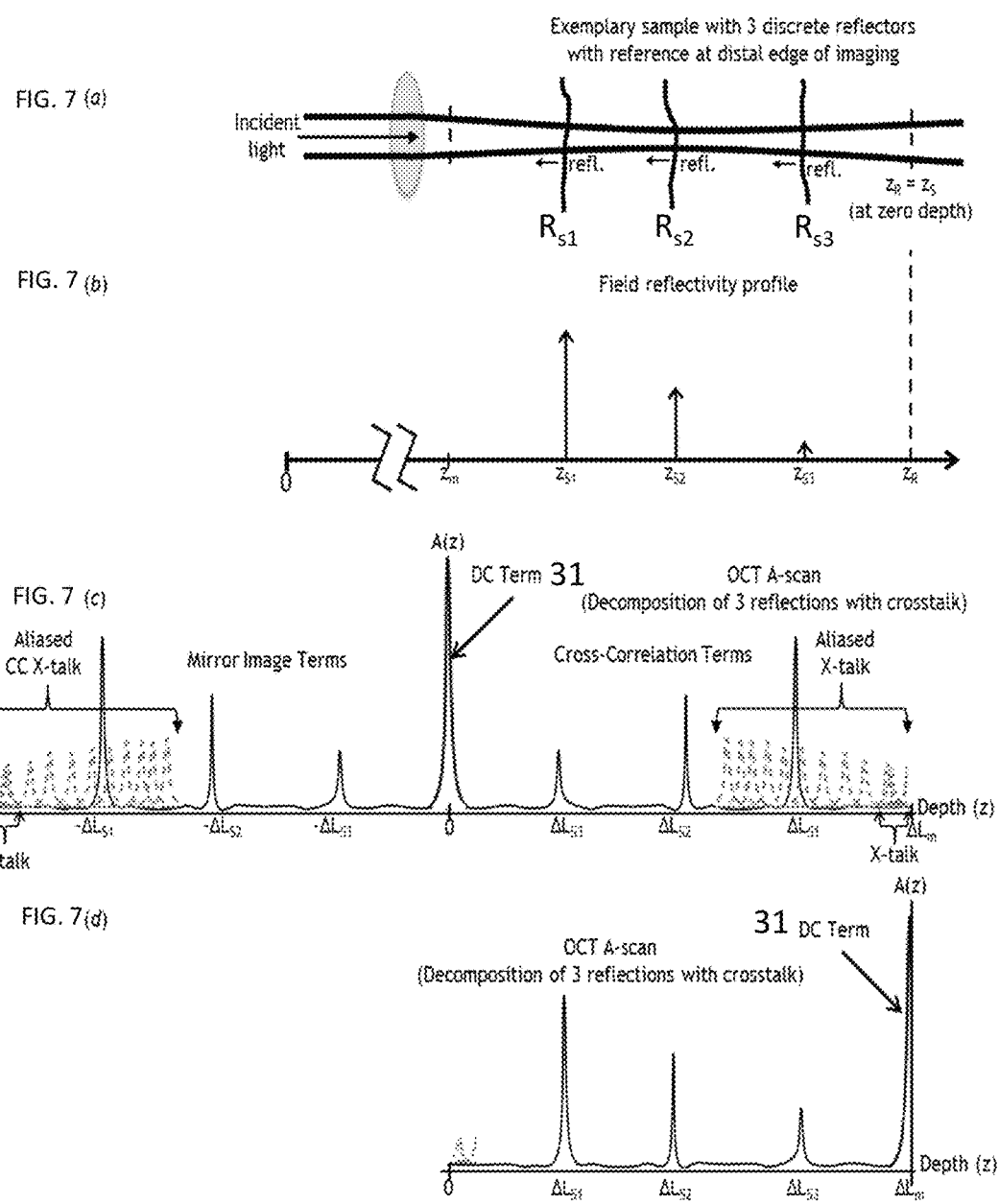

In one or more embodiments, a reference arm may be placed at the distal edge of the FOV (for example, at a predetermined depth, a maximum desired depth, etc.), such as the embodiment shown in FIGS. 6(a)-7(d), crosstalk noise artifacts no longer overlap about DC but rather alias (e.g., the signal will flip, higher frequency signals will mirror image around or about the Nyquist frequency) about the Nyquist frequency (see e.g., FIG. 7(c)). For instance, a multimodality OCT system employing a double clad fiber segment where the reference reflection for the OCT modality is positioned at about the distal edge of the FOV (i.e., the optical path length of the reference reflection is longer that the sample reflections and is situated at about the length of the maximum desired sample reflection) may be used as one example of the first embodiment.

FIGS. 6(a)-6(d) show an exemplary sample reflectivity profile having three discrete reflectors with the reference reflection at the end of image FOV (see FIGS. 6(a) and 6(b)), an A-scan from the Fourier domain low coherence interferometry in the absence (or substantial absence) of crosstalk (FIG. 6(c)) and a resultant A-scan in the absence (or substantial absence) of crosstalk (FIG. 6(d)). This is advantageous since most of the crosstalk noise is now beyond the desired imaging FOV and therefore may be filtered out without affecting the desired signal, as shown in FIG. 7(d). FIGS. 7(a)-7(d) show an exemplary sample reflectivity profile having three discrete reflectors with the reference reflection at the end of image FOV (see FIGS. 7(a) and 7(b)), an A-scan from the Fourier domain low coherence interferometry in the presence of crosstalk (FIG. 7(c)) and a resultant A-scan in the presence of crosstalk with added filtering at and beyond $z_{max}$ (FIG. 7(d)). In addition to the added anti-aliasing filtering, in one or more embodiments, signals near to and beyond the Nyquist frequency are reduced in amplitude due to the coherence roll-off effect (i.e., the further away from DC 31, the larger the signal amplitude drop from the coherence effect) and detection bandwidth. FIG. 7(d) shows the substantially reduced and almost completely eliminated crosstalk noise from the same exemplary field reflectivity profile with similar crosstalk strength as that shown in the aforementioned method depicted in FIGS. 5(a)-5(d). The method(s) shown in FIGS. 6(a)-7(d), referred to herein as the complex conjugate method, involve the added step of flipping the z-axis array so as to properly capture the depth relationship (see e.g., FIGS. 6(d) and 7(d)). An added feature of this method is that the DC artifact is nearer to the distal edge of the imaging FOV instead of the start of the FOV where strong and important signals may be overshadowed by the DC artifact. One may further filter the DC artifact without worrying about the image signal since most of the image content should be further from DC in one or more embodiments. A bandpass filter may be used, for example, to both filter the DC artifact and signals beyond the Nyquist frequency. Filtering may be done electronically to eliminate or reduce any crosstalk that might potentially alias into the desired signal frequency range. Analog filtering may be a low pass filter to eliminate or reduce aliasing or may be a high pass filter to eliminate or reduce the DC artifact. The analog filter may be a bandpass filter with a certain order for the low frequency cutoff and a certain order for the high frequency cutoff.

Figures 8A, 8B:
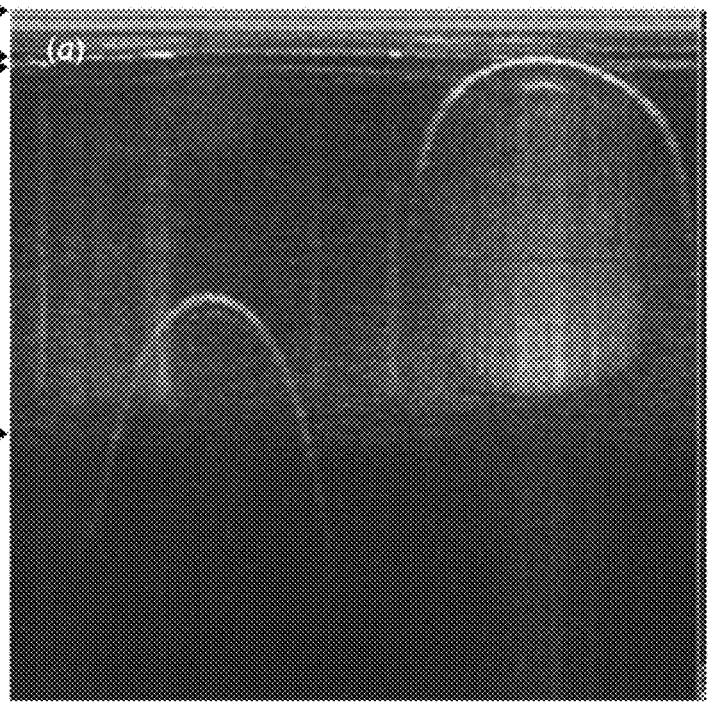
FIGS. 8(a)-8(b) are images acquired using at least one embodiment of an intravascular OCT system employing a rotating DCF catheter probe using the image acquisition method of FIGS. 4(a)-5(d) and using the complex conjugate method of FIGS. 6(a)-7(d), respectively, in accordance with one or more aspects of the present disclosure.
Figure 9:
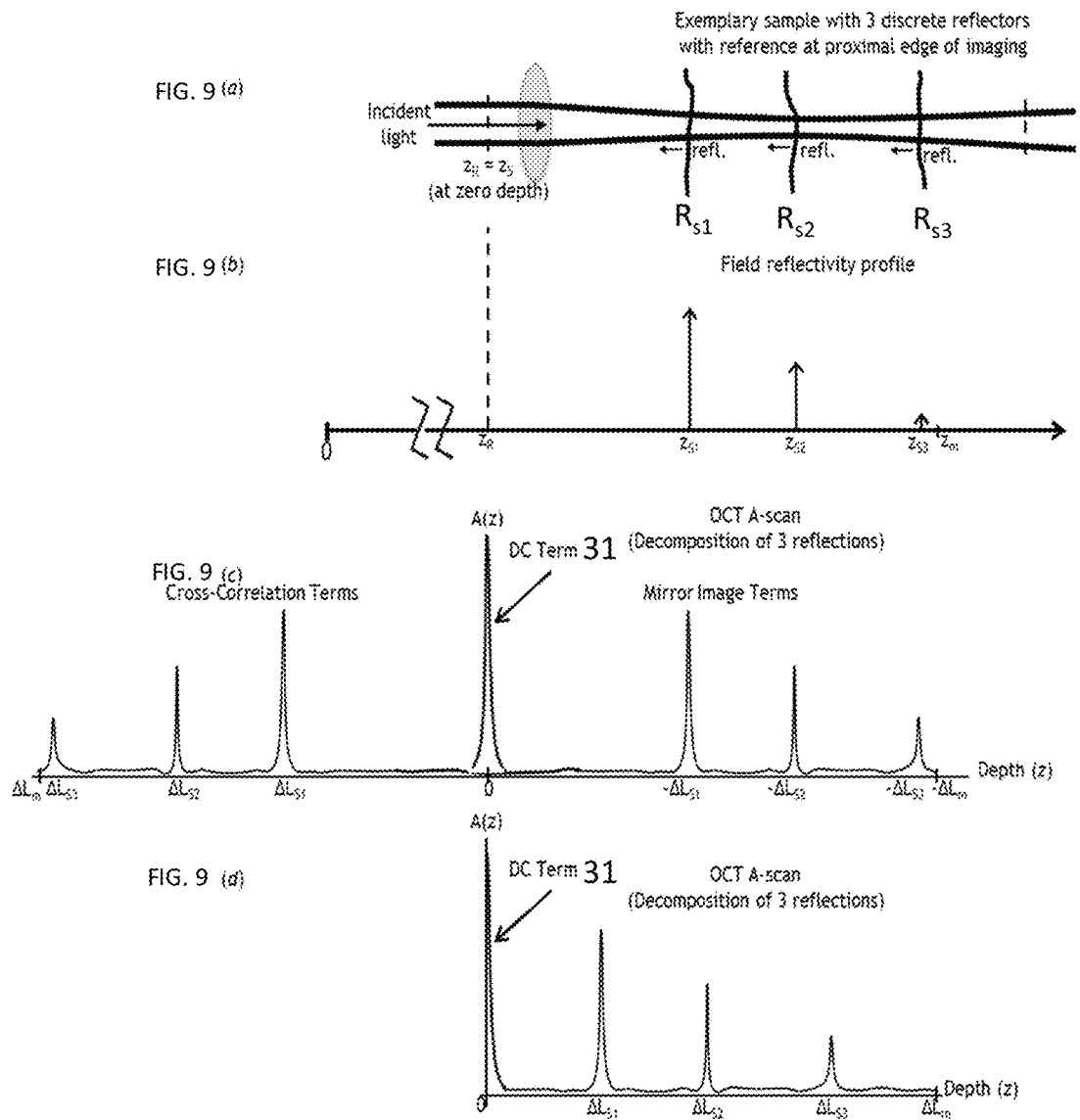

In one or more embodiments involving intravascular OCT, utilizing a DCF catheter probe, the reflection from the catheter sheath outer layer is placed such that it corresponds to actual catheter radius and as such reflections from the sheath and catheter distal optics are located close to the zero reflectivity position. The sheath and catheter optics being strong reflectors bring about several crosstalk noise artifacts that fold about DC, due to the complex conjugate effect, and end up overlapping with the desired image. FIGS. 8(a)-8(b) show a comparison between the method relating to FIGS. 4(a)-5(d) as aforementioned (see FIG. 8(a) on the left side) and the complex conjugate method relating to FIGS. 6(a)-7(d) (see FIG. 8(b) on the right side). The imaged sample is of a pair of stainless steel tweezers with each tip at a different depth from the catheter. The images were acquired using an intravascular OCT system employing a rotating DCF catheter probe using the methods discussed for FIGS. 8(a) and 8(b). As can be seen from FIG. 8(a), the method of FIGS. 4(a)-5(d) suffers from substantial crosstalk noise, which overlaps a sizeable portion of the image. At least one embodiment of the complex conjugate method of the present disclosure on the other hand, as seen in FIG. 8(b), shows a crosstalk noise-free image with DC and auto-correlation artifacts on opposing ends of the catheter probe reflections allowing for a clear visualization of the catheter reflections.

Second Embodiment—Shift Method

Figure 10:
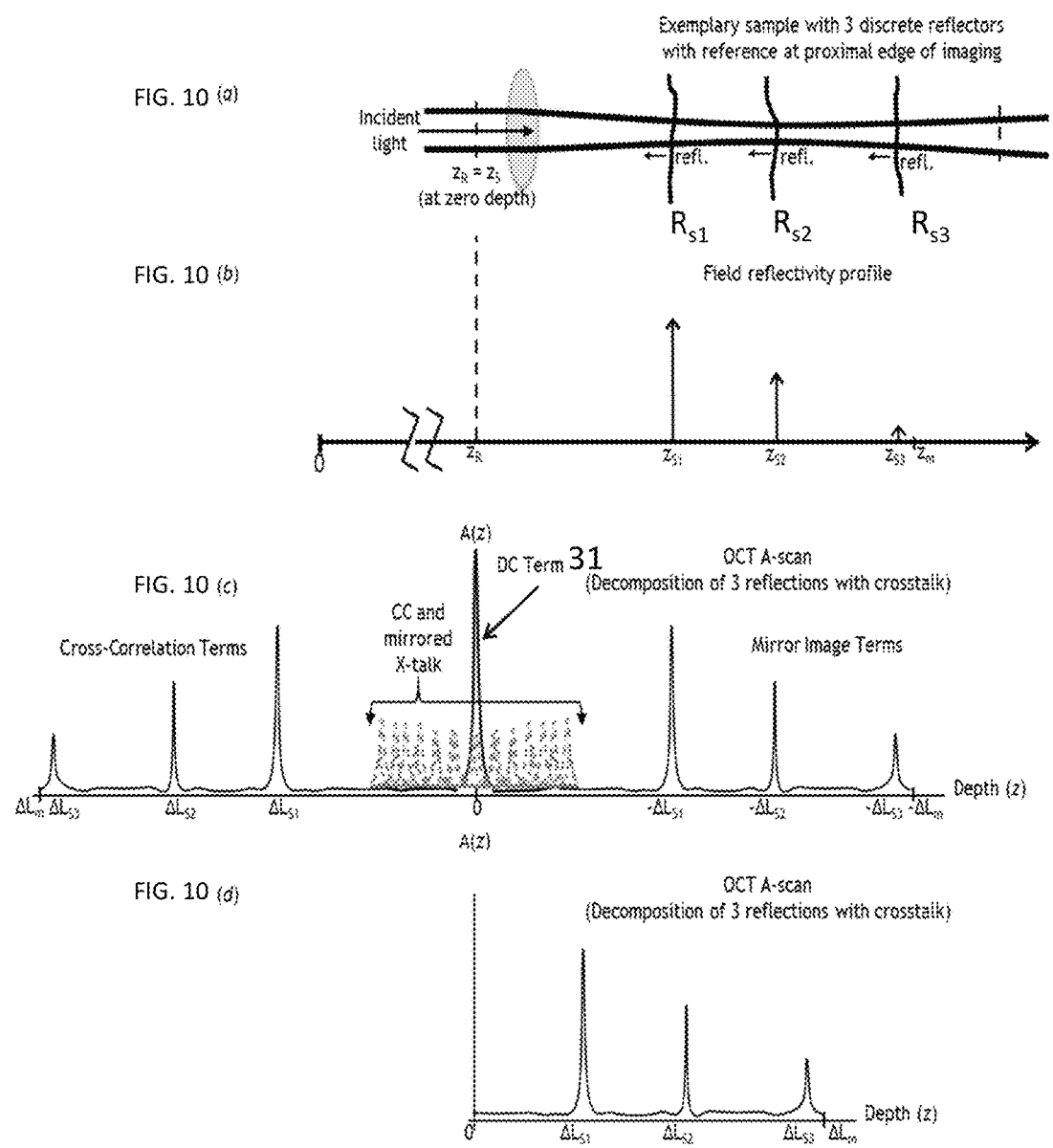

Another method for reducing crosstalk involves placing the reference arm (see $Z_R$) at a shorter distance than the proximal edge of the image FOV, (see FIGS. 9(a)-10(d)), in which case, even though crosstalk noise wraps about DC it no longer lands in the desired imaging range (see e.g., FIG. 10(c)). For instance, a multimodality OCT system employing a double clad fiber segment where the reference reflection for the OCT modality is positioned at a shorter optical path length than the proximal edge of the FOV (i.e., the optical path length of the reference reflection is shorter than the first desired sample reflection such that crosstalk noise wraps about DC and is no longer in the desired imaging range) may be used as one example of the second embodiment.

FIGS. 9(a)-(d) show an exemplary sample reflectivity profile having three discrete reflectors with the reference reflection shorter than the desired start of the image FOV (see FIGS. 9(a)-9(b)), an A-scan from the Fourier domain low coherence interferometry in the absence (or substantial absence) of crosstalk (FIG. 9(c)) and a resultant A-scan in the absence (or substantial absence) of crosstalk after digital cropping and flipping of the depth array (FIG. 9(d)). This is advantageous since most of the crosstalk noise is now beyond the desired imaging FOV and therefore may be filtered out without affecting the desired signal, as shown in FIG. 10(d). FIGS. 10(a)-10(d) show an exemplary sample reflectivity profile having three discrete reflectors with the reference reflection shorter than the desired start of the image FOV (see FIGS. 10(a) and 10(b)), an A-scan from the Fourier domain low coherence interferometry in the presence of crosstalk (FIG. 10(c)) and a resultant A-scan in the presence of crosstalk after digital cropping and flipping of the depth array (FIG. 10(d)). Placing the reference arm may be done in such a way so as to have about half of the crosstalk noise extend beyond DC 31, wrap-around, and still be away from the desired image signal; resulting in a crosstalk free imaging region albeit with a smaller FOV than the starting FOV. The crosstalk noise laden region may then be digitally cropped (e.g., to have an image of the desired sample without any noise artifact) and the catheter probe location adjusted to reflect true physical depth of the probe as shown, for example, in FIG. 10(d). While a reduced useable FOV may occur, in one or more embodiments, such a situation may be compensated for by starting with a FOV equal to the desired FOV plus an anticipated cropped region. The cropped image may be further adjusted by putting black pixels where DC artifact was and with the correct number of pixels so as to have the sample appear with accurate dimensions. In one or more embodiments, the added pixels are such that they represent the lower range of intensities displayed in the same color map as the whole image. The added pixels may be such that they have similar characteristics (e.g., noise, speckle, etc.) as the image background. The number of added pixels may be such that if a catheter of certain dimension is used the actual size measured from the image reflects the actual physical dimension of the catheter.

FIGS. 11(a)-11(f) show a comparison between the aforementioned method of FIGS. 4(a)-5(d) (see FIGS. 11(a) and

Figure 11:
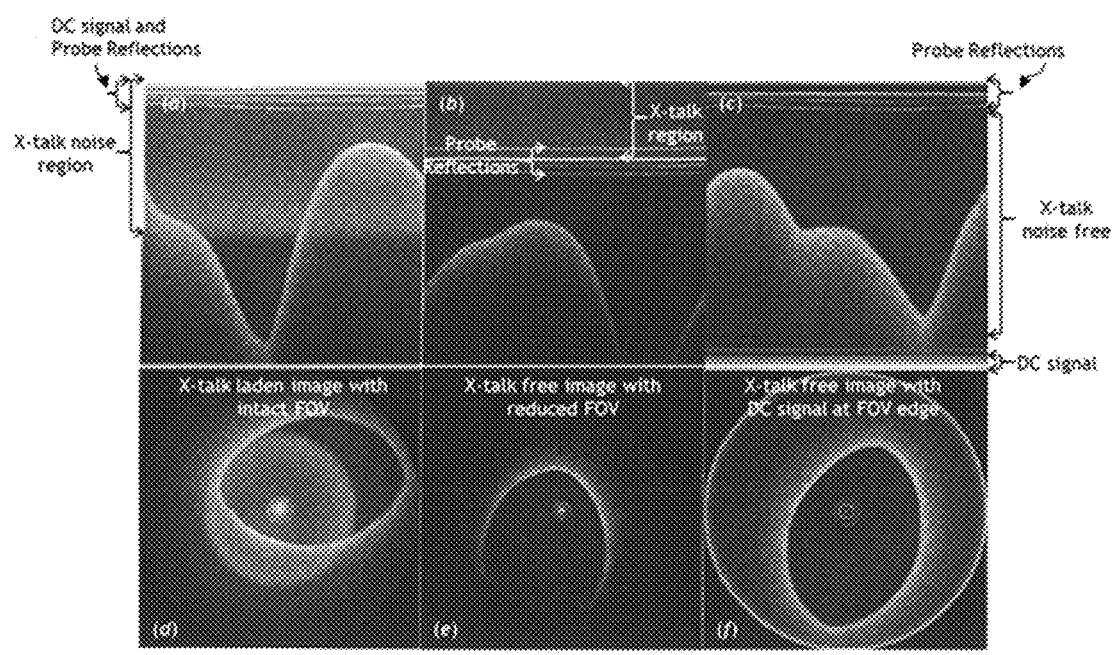
FIGS. 11(a)-11(f) are images acquired using at least one embodiment of an intravascular OCT system employing a rotating DCF catheter probe using the image acquisition method of FIGS. 4(a)-5(d) (see FIGS. 11(a) and 11(d)), using the complex conjugate method of FIGS. 6(a)-7(d) (see FIGS. 11(c) and 11(f)) and using the shift method of FIGS. 9(a)-10(d) (see FIGS. 11(b) and 11(e)) in accordance with one or more aspects of the present disclosure.

11(*d*)), the complex conjugate method (see FIGS. 11(*b*) and 11(*e*)), and the shift method (see FIGS. 11(*c*) and 11(*f*)) acquired using the same MMOCT system and rotating DCF catheter probe described earlier, with FIGS. 11(*a*)-11(*c*) being displayed in the polar coordinate system and FIGS. 11(*d*)-11(*f*) being displayed in the Cartesian coordinate system. FIGS. 11(*a*)-11(*f*) are images of a tubular vessel tissue mimicking phantom acquired using the intravascular OCT system employing the rotating DCF catheter. As can be seen results obtained using the aforementioned method of FIGS. 4(*a*)-5(*d*) show substantial crosstalk that completely overlaps a substantial portion of the image (see FIGS. 11(*a*) and 11(*d*)). The shift method results in crosstalk noise being completely contained in the undesired portion of the image (see FIGS. 11(*b*) and 11(*e*)), and digitally removed as in FIG. 11(*e*). The complex conjugate method on the other end shows completely eliminated crosstalk noise with the DC noise being pushed to the end edge of the image FOV (see FIGS. 11(*c*) and 11(*f*)).

As shown in FIG. 2, the catheter 120 may be disposed or positioned in a sheath 121. The sheath 121 may be transparent or semitransparent, may be extruded, and may be single or multilayer. In one or more embodiments, the sheath 121 may be employed with a probe in any application, such as, but not limited to, an OCT needle, an OCT capsule, etc. The catheter 120 is used with the sheath 121 for illustrative purposes, and any probe or catheter may be used with the sheath 121 and/or OCT techniques discussed herein.

Figure 12A:
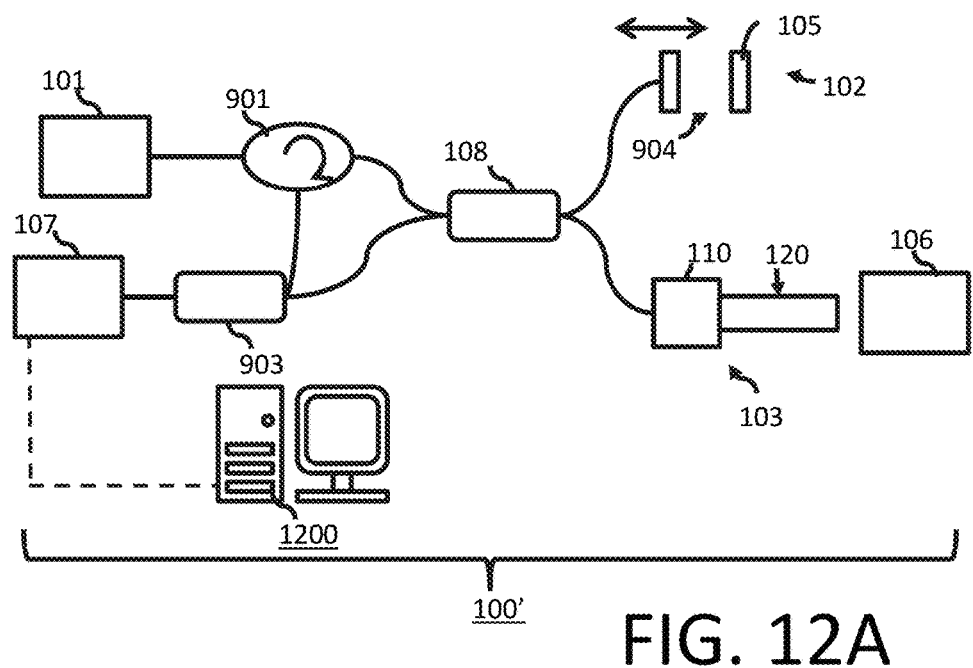
FIG. 12A illustrates a schematic diagram of an optical system that may be used with at least one embodiment of a crosstalk mitigation or elimination OCT technique for a bench-top, such as, but not limited to ophthalmic applications in accordance with one or more aspects of the present disclosure.

In accordance with one or more further aspects of the present disclosure, bench top systems may be utilized with the crosstalk elimination or mitigation OCT techniques disclosed herein. FIG. 12A shows an example of a system that can utilize the crosstalk elimination or reduction OCT techniques for a bench-top such as for ophthalmic applications. A light from a light source 101 delivers and splits into a reference arm 102 and a sample arm 103 with a deflecting section 108. A reference beam goes through a length adjustment section 904 and is reflected from a reference mirror (such as reference mirror or reference reflection 105 shown in FIG. 1) in the reference arm 102 while a sample beam is reflected or scattered from a sample 106 in the sample arm 103 (e.g., via the PIU 110 and the catheter 120). In one embodiment, both beams combine at the deflecting section 108 and generate interference patterns. In one or more embodiments, the beams go to the combiner 903, and the combiner 903 combines both beams via the circulator 901 and the deflecting section 108, and the combined beams are delivered to one or more detectors (such as the one or more detectors 107). The output of the interferometer is continuously acquired with one or more detectors, such as the one or more detectors 107. The electrical analog signals are converted to the digital signals to analyze them with a computer, such as, but not limited to, the computer 1200 (see FIG. 12A; also shown in FIG. 13 discussed further below), the computer 1200' (see e.g., FIG. 14 discussed further below), etc.

Figure 12B:
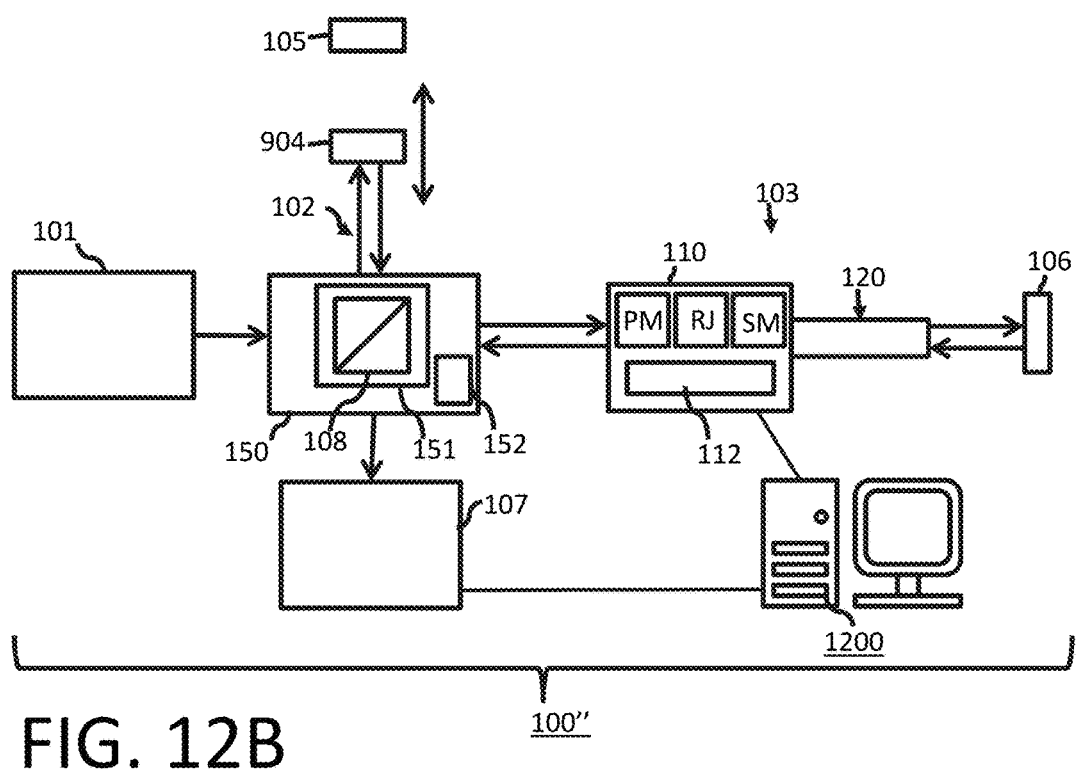
FIG. 12B illustrates a schematic diagram of another optical system that may be used with at least one embodiment of a crosstalk mitigation or elimination OCT technique for a bench-top, such as, but not limited to ophthalmic applications in accordance with one or more aspects of the present disclosure.

In accordance with one or more further aspects of the present disclosure, one or more other systems may be utilized with the crosstalk elimination or mitigation OCT techniques disclosed herein. FIG. 12B shows an example of a system 100" that may utilize the crosstalk elimination or reduction OCT techniques such as for ophthalmic applications. A light from a light source 101 delivers and splits into a reference arm 102 and a sample arm 103 with a deflecting section 108 (e.g., a beamsplitter or other deflecting or deflected section discussed herein) located inside of an OCT imaging engine 150, which may also include an OCT interferometer 151 (which may house or include the deflecting section 108) and a swept source engine 152 in one or more embodiments. A reference beam may through a length adjustment section 904, which may operate to change the distance of a reference mirror (such as reference mirror or reference reflection 105; also shown in FIG. 1) and is reflected from the reference reflection 105 in the reference arm 102 while a sample beam is reflected or scattered from a sample 106 in the sample arm 103. In one embodiment, both beams combine at the deflecting section 108 and generate interference patterns. In one or more embodiments, the combined beams are delivered to one or more detectors. The output of the interferometer 151 is continuously acquired with one or more detectors, such as the one or more detectors 107. The electrical analog signals are converted to the digital signals to analyze them with a computer, such as, but not limited to, the computer 1200 (see FIG. 12B; also shown in FIG. 13 discussed further below), the computer 1200' (see e.g., FIG. 14 discussed further below), etc. In one or more embodiments, the sample arm 130 includes the PIU 110 and the catheter 120 so that the sample beam is reflected or scattered from the sample 106 as discussed herein. In one or more embodiments, the PIU 110 may include one or more motors to control the pullback operation of the catheter 120 (or one or more components thereof) and/or to control the rotation or spin of the catheter 120 (or one or more components thereof). For example, the PIU 110 may include a pullback motor (PM) and a spin motor (SM), and/or may include a motion control unit 112 that operates to perform the pullback and/or rotation features using the pullback motor PM and/or the spin motor SM. As discussed herein, the PIU 110 may include a rotary junction (e.g., rotary junction RJ as shown in FIG. 12B). The rotary junction RJ may be connected to the spin motor SM so that the catheter 120 may obtain one or more views or images of the sample 106. The computer 1200 (or the computer 1200') may be used to control one or more of the pullback motor PM, the spin motor SM and/or the motion control unit 112. An OCT system may include one or more of the OCT engine 150, a computer (e.g., the computer 1200, the computer 1200', etc.), the PIU no, the catheter 120, a monitor, etc. One or more embodiments of an OCT system may interact with one or more external systems, such as, but not limited to, an angio system, external displays, one or more hospital networks, external storage media, a power supply, a bedside controller (e.g., which may be connected to the OCT system using Bluetooth technology or other methods known for wireless communication), etc.

Unless otherwise discussed herein, like numerals indicate like elements. For example, while variations or differences exist between the position of the reference reflection 105 (and/or reference arm 102) depending on the OCT method(s) being employed to reduce or eliminate crosstalk noise, one or more features thereof may be the same or similar to each other, such as, but not limited to, the deflecting section 108 or other component(s) thereof. Those skilled in the art will appreciate that the system 100, and/or one or more elements thereof (e.g., the deflecting section 108; the reference arm 102; the sample arm 103; etc.), may operate in the same or similar fashion to the system 100' and/or the system 100", and/or those like-numbered elements of the system 100' and/or of the system 100", as discussed above or any additional like-numbered elements discussed further herein below. Those skilled in the art will appreciate the other alternative embodiments of the system 100', and/or one or more like-numbered elements thereof (e.g., the deflecting section 108, the reference arm 102, the sample arm 103, etc.), while having other variations as discussed herein, may operate in the same or similar fashion to the like-numbered elements of any of the other systems discussed herein, such as, but not limited to, the system 100 and/or the system 100", or catheter 120 discussed herein. Indeed, while certain differences exist between the systems 100, 100', and 100" as aforementioned, there are many similarities between the systems 100, 100', and 100".

There are many ways to compute power and/or eliminate, reduce or minimize cross talk, digital as well as analog. In at least one embodiment, a computer may be dedicated to the control and the monitoring of the OCT devices, systems, methods and/or storage mediums described herein.

Figure 13:
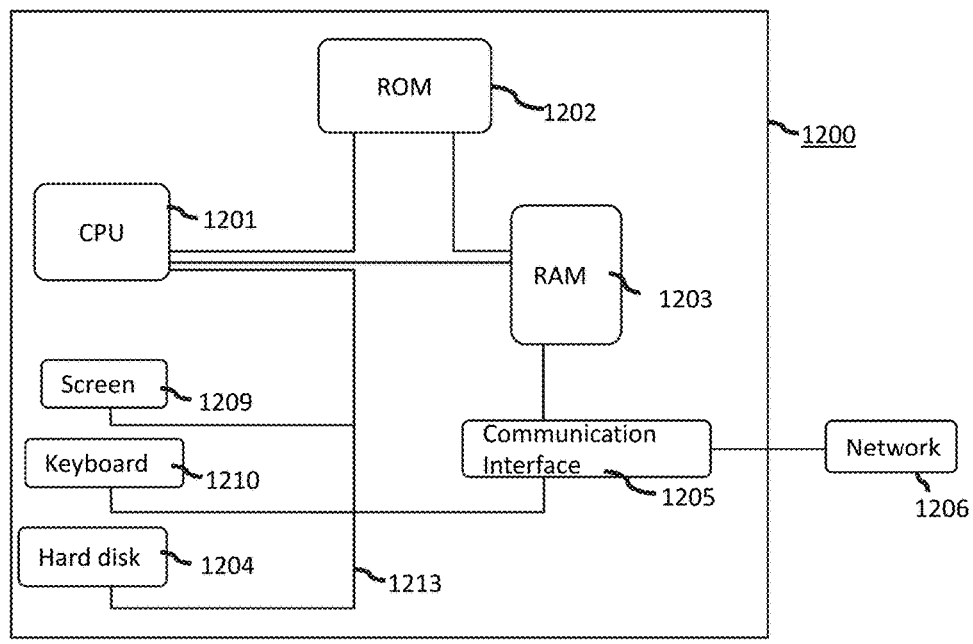
FIG. 13 shows a schematic diagram of an embodiment of a computer that may be used with one or more embodiments of a crosstalk mitigation or elimination OCT technique(s) in accordance with one or more aspects of the present disclosure.

Various components of a computer system 1200 are provided in FIG. 13. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 13). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a system, such as the system 100 discussed herein above, via one or more lines 1213), and one or more other computer systems 1200 may include one or more combinations of the other aforementioned components. The CPU 1201 is configured to read and perform computer-executable instructions stored in a storage medium. The computer-executable instructions may include those for the performance of the methods and/or calculations described herein. The system 1200 may include one or more additional processors in addition to CPU 1201, and such processors, including the CPU 1201, may be used for crosstalk reduction or elimination. The system 1200 may further include one or more processors connected via a network connection (e.g., via network 1206). The CPU 1201 and any additional processor being used by the system 1200 may be located in the same telecom network or in different telecom networks (e.g., performing crosstalk reduction or elimination may be controlled remotely).

The I/O or communication interface 1205 provides communication interfaces to input and output devices, which may include the light source 101, a spectrometer, a microphone, a communication cable and a network (either wired or wireless), a keyboard 1210, a mouse, a touch screen or screen 1209, a light pen and so on. The Monitor interface or screen 1209 provides communication interfaces thereto.

Any methods and/or data of the present disclosure, such as the methods for performing crosstalk reduction or elimination via OCT as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-Ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive, SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 1200, etc., as described above may be achieved utilizing suitable hardware, such as that illustrated in the figures. Functionality of one or more aspects of the present disclosure may be achieved utilizing suitable hardware, such as that illustrated in FIG. 13. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 13) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components. Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

Figure 14:
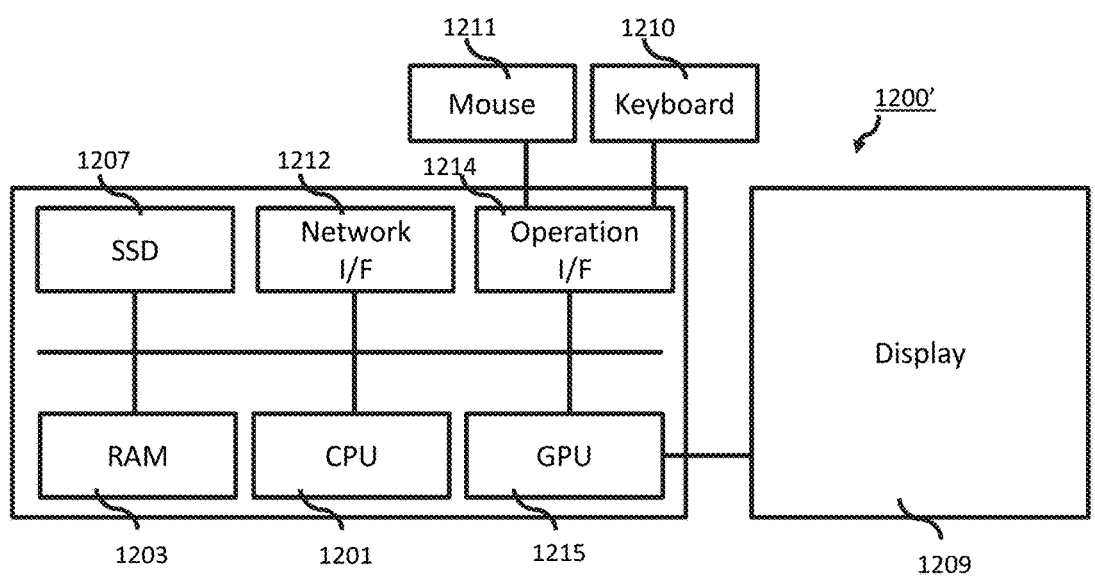
FIG. 14 shows a schematic diagram of an alternative embodiment of a computer that may be used with one or more embodiments of a crosstalk mitigation or elimination OCT technique(s) in accordance with one or more aspects of the present disclosure.

As aforementioned, hardware structure of an alternative embodiment of a computer or console 1200' is shown in FIG. 14. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. Preferably, the computer or console 1200' includes a display 1209. The computer 1200' may connect with the rotary junction, a motion control unit and/or one or more motors via the operation interface 1214 or the network interface 1212. A computer, such as the computer 1200', may include the MCU in one or more embodiments. The operation interface 1214 is connected with an operation unit such as a mouse device 1211, a keyboard 1210 or a touch panel device. The computer 1200' may include two or more of each component. Alternatively, the CPU 1201 or the GPU 1215 may be replaced by the field-programmable gate array (FPGA), the application-specific integrated circuit (ASIC) or other processing unit depending on the design of a computer, such as the computer 1200, the computer 1200', etc.

A computer program is stored in the SSD 1207, and the CPU 1201 loads the program onto the RAM 1203, and executes the instructions in the program to perform one or more processes described herein, as well as the basic input, output, calculation, memory writing and memory reading processes.

The computer, such as the computer 1200, 1200', may communicate with the PIU 110 (and/or a rotary junction and/or at least one motor being used therewith) and one or more other components of a system, such as the system 100, 100', 100", etc. to perform imaging, and constructs or reconstructs an image from the acquired data. The monitor or display 1209 displays the constructed or reconstructed image, and may display other information about the object to be imaged. The monitor 1209 may also provide a graphical user interface for a user to operate an OCT system (e.g., the system 100, the system 100', the system 100", etc.). An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs the system (e.g., the system 100, the system 100', the system 100", etc.) to set, change, start or end the imaging. The laser source 101 and any other component of the systems discussed herein may have interfaces to communicate with the computers 1200, 1200' to send and receive status information and the control signals.

The present disclosure and/or one or more components of devices, systems and storage mediums, and/or methods, thereof also may be used in conjunction with any suitable optical assembly or OCT probes including, but not limited to, arrangements and methods for providing multimodality microscopic imaging of one or more biological structure, such as those disclosed in U.S. Pat. Nos. 7,872,759; 8,289, 522; and U.S. Pat. No. 8,928,889 to Tearney et al. and arrangements and methods of facilitating photoluminescence imaging, such as those disclosed in U.S. Pat. No. 7,889,348 to Tearney et al., as well as disclosures directed to multimodality imaging disclosed in U.S. Pat. No. 9,332,942 and U.S. Patent Publication Nos. 2009/0192358, 2010/0092389, 2012/0101374 and 2016/0228097, each of which patents and patent publications are incorporated by reference herein in their entireties.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

The invention claimed is:

1. A crosstalk elimination or mitigation optical coherence tomography (OCT) system, the system comprising:
    an interference optical system that operates to: (i) receive and divide light from a light source into a first light with which an object or sample is to be irradiated and which travels along a sample arm of the interference optical system and a second reference light, (ii) send the second reference light along a reference arm of the interference optical system for reflection off of a reference reflection of the interference optical system, and (iii) generate interference light by causing reflected or scattered light of the first light with which the object or sample has been irradiated and the reflected second reference light to combine or recombine, and/or to interfere, with each other, the interference light generating one or more interference patterns; and
    at least one detector that operates to continuously acquire the interference light and/or the one or more interference patterns to measure the interference or the one or more interference patterns between the combined or recombined light,
    wherein the reference reflection is positioned in, at, at about, or around a field of view such that crosstalk noise is mitigated or eliminated from the field of view, and
    wherein:
    (i) the reference reflection is positioned at, at about, or around one or more of:
        (a) a distal edge or an end of the field of view; and
        (b) a distal edge or an end of the field of view such that an optical path length of the reference reflection is longer than a reflection or reflections of the object or sample and is situated at or at about a length of a maximum predetermined object or sample reflection; or
    (ii) the reference reflection is positioned at, at about, or around one or more of:
        (a) a position that is shorter than a predetermined or determined start of, or shorter than a proximal edge of, the field of view;
        (b) a position that is shorter than a predetermined or determined start of, or shorter than a proximal edge of, the field of view such that an optical path length of the reference reflection is shorter than a first predetermined or determined sample reflection; and
        (c) a position that is shorter than a predetermined or determined start of, or shorter than a proximal edge of, the field of view such that: (i) an optical path length of the reference reflection is shorter than a first predetermined or determined sample reflection, and (ii) the crosstalk noise wraps about a DC position and is no longer in a predetermined imaging range of the field of view.

2. The OCT system of claim 1, wherein the OCT system is a multimodality OCT system and includes a double-clad fiber (DCF) segment, and the OCT system operates to eliminate or mitigate crosstalk induced image artifacts in coherent application(s) requiring use of the DCF segment.

3. The OCT system of claim 1, further comprising a filter to perform analog, digital or electronic filtering to eliminate or reduce any crosstalk noise that would otherwise alias into a predetermined signal frequency range.

4. The OCT system of claim 3, wherein the filter may include at least one of:
(i) a low pass filter to eliminate or reduce the aliasing;
(ii) a high pass filter to eliminate or reduce direct current (DC) artifact(s); and
(iii) a bandpass filter with a certain predetermined order for a low frequency cutoff and a certain order for a high frequency cutoff.

5. The OCT system of claim 1, further comprising at least one of:
(i) the light source that operates to produce the light; and
(ii) a guide or waveguide for transmitting the light from the light source.

6. The OCT system of claim 1, further comprising a deflecting section that operates to deflect the light from the light source to the interference optical system, and then send light received from the interference optical system towards the at least one detector.

7. The OCT system of claim 6, wherein the deflecting section comprises at least one of: one or more interferometers, a circulator, a beam splitter, an isolator, a coupler, a fusion fiber coupler, a partially severed mirror with holes therein, and a partially severed mirror with a tap.

8. The OCT system of claim 1, further comprising an adjustment section that operates to control one or more relative optical characteristics between the first light having illuminated the object or sample and the reflected second light, and a deflecting section that operates to pass the reflected second light from the adjustment section and towards the at least one detector.

9. The OCT system of claim 1, further comprising at least one processor that operates to process a signal from the at least one detector to acquire information of the object or sample.

10. A method for performing crosstalk noise mitigation or elimination using an optical coherence tomography (OCT) device or system having an interference optical system that operates to generate interference light and one or more interference patterns from a light that has been split into a first light with which an object or sample has been irradiated and a second reference light and having at least one detector, the method comprising:
positioning a reference reflection of the interference optical system in, at, at about, or around a field of view such that crosstalk noise is mitigated or eliminated from the field of view,
wherein the positioning step further comprises:
(i) positioning the reference reflection at, at about, or around one or more of:
(a) a distal edge or an end of the field of view; and
(b) a distal edge or an end of the field of view such that an optical path length of the reference reflection is longer than a reflection or reflections of the object or sample and is situated at or at about a length of a maximum predetermined object or sample reflection; or (ii) positioning the reference reflection at, at about, or around one or more of:
(a) a position that is shorter than a predetermined or determined start of, or shorter than a proximal edge of, the field of view;
(b) a position that is shorter than a predetermined or determined start of, or shorter than a proximal edge of, the field of view such that an optical path length of the reference reflection is shorter than a first predetermined or determined sample reflection; and
(c) a position that is shorter than a predetermined or determined start of, or shorter than a proximal edge of, the field of view such that: (i) an optical path length of the reference reflection is shorter than a first predetermined or determined sample reflection, and (ii) the crosstalk noise wraps about a DC position and is no longer in a predetermined imaging range of the field of view.

11. The method of claim 10, wherein the OCT device or system is a multimodality OCT device or system and includes a double-clad fiber (DCF) segment, and the OCT device or system operates to eliminate or mitigate crosstalk induced image artifacts in coherent application(s) requiring use of the DCF segment.

12. The method of claim 10, further comprising performing analog, digital or electronic filtering to eliminate or reduce any crosstalk noise that would otherwise alias into a predetermined signal frequency range.

13. The method of claim 10, further comprising positioning the reference reflection such that about half of the crosstalk noise extends beyond the DC position, wraps around and is still away from a predetermined imaging range of the field of view and/or a predetermined image signal resulting in a crosstalk free region of an image of the object or sample.

14. The method of claim 13, further comprising cropping a crosstalk noise laden region of the image digitally to have or obtain an image of the object or sample without any noise artifact(s).

15. The method of claim 14, wherein at least one of:
(i) the cropped image is further adjusted by putting black pixels where a DC artifact is or was and with a predetermined or determined number of pixels so as to have the object or sample appear with accurate dimensions in the image;
(ii) the added pixels are such that the pixels represent a lower range of intensities displayed in a same color map as the whole image;
(iii) the added pixels are such that the pixels have similar or the same characteristics as a background of the image;
(iv) the similar or the same characteristics include at least one of noise and speckle; and
(v) a number of the added pixels is such that, in response to using a catheter of a predetermined or determined dimension, an actual size measured from the image reflects an actual physical dimension of the catheter.

* * * * *